(12) United States Patent
Weng et al.

(10) Patent No.: US 11,708,388 B2
(45) Date of Patent: Jul. 25, 2023

(54) USES OF A SAPONIN AND METHOD FOR ITS ISOLATION

(71) Applicant: Freie Universität Berlin, Berlin (DE)

(72) Inventors: Alexander Weng, Berlin (DE); Matthias F. Melzig, Berlin (DE); Simko Sama, Berlin (DE)

(73) Assignee: Freie Universität Berlin, Berlin (DE)

( * ) Notice: Subject to any disclaimer, the term of this patent is extended or adjusted under 35 U.S.C. 154(b) by 441 days.

(21) Appl. No.: 16/628,838

(22) PCT Filed: Jul. 10, 2018

(86) PCT No.: PCT/EP2018/068663
§ 371 (c)(1),
(2) Date: Jan. 6, 2020

(87) PCT Pub. No.: WO2019/011914
PCT Pub. Date: Jan. 17, 2019

(65) Prior Publication Data
US 2020/0131219 A1  Apr. 30, 2020

(30) Foreign Application Priority Data

Jul. 11, 2017 (EP) .................................. 17180730
Jan. 18, 2018 (EP) .................................. 18152304

(51) Int. Cl.
*C07H 15/256* (2006.01)
*A61K 47/26* (2006.01)
*C12N 15/87* (2006.01)

(52) U.S. Cl.
CPC .......... *C07H 15/256* (2013.01); *A61K 47/26* (2013.01); *C12N 15/87* (2013.01)

(58) Field of Classification Search
None
See application file for complete search history.

(56) References Cited

FOREIGN PATENT DOCUMENTS

| CN | 1046887988 A | 6/2015 |
| JP | 2004528321 A | 9/2004 |
| WO | 02/080981 A2 | 10/2002 |

OTHER PUBLICATIONS

Alexander Weng et al: "Saponins modulate the intracellular trafficking of protein toxins", Journal of Controlled Release, vol. 164, No. 1, Nov. 1, 2012, pp. 74-86.
Alexander Weng et al: "Improved intracellular delivery of peptide- and lipid-nanoplexes by natural glycosides", Journal of Controlled Release, vol. 206, May 1, 2015, pp. 75-90.
Weng et al: "A convenient method for saponin isolation in tumour therapy", Journal of Chromatography B: Biomedical Sciences & Applications, Elsevier, Amsterdam, NL, vol. 878, No. 7-8, Mar. 1, 2010, pp. 713-718.
Mayank Thakur et al: "High-speed countercurrent chromatographic recovery and off-line electrospray ionization mass spectrometry profiling of bisdesmodic saponins from Saponaria officinalis possessing synergistic toxicity enhancing properties on targeted anti-tumor toxins", Journal of Chromatography B: Biomedical Sciences & Applications, vol. 955, Feb. 19, 2014, pp. 1-9.
Zhonghua Jia et al: "Major Triterpenoid Saponins from Saponaria officinalis", Journal of Natural Products., vol. 61, No. 11, Nov. 1, 1998, pp. 1368-1373.
Mohamed Haddad et al: "New Triterpene Saponins from Acanthophyllum pachystegium", Helvetica Chimica Acta, vol. 87, Jan. 1, 2004, pp. 73-81.
Hongzheng Fu et al: "Silenorubicosides A-D, Triterpenoid Saponins from Silene rubicunda", Journal of Natural Products, vol. 68, No. 5, May 1, 2005, pp. 754-758.
Barbara Moniuszko-Szajwaj et al: "Highly Polar Triterpenoid Saponins from the Roots of Saponaria officinalis L.", Helvetica Chimica Acta, vol. 99, No. 5, May 1, 2016, pp. 347-354.
Hendrik Fuchs et al: "Glycosylated Triterpenoids as Endosomal Escape Enhancers in Targeted Tumor Therapies", Biomedicines, vol. 5, No. 2, Mar. 29, 2017, p. 14.
Sama Simko et al: "Sapofectosid—Ensuring non-toxic and effective DNA and RNA delivery", International Journal of Pharmaceutics, vol. 534, No. 1, Oct. 17, 2017, pp. 195-205.
Haddad, M. et al., New Triterpene Saponins from Acanthophyllum pachystegium, Helvetica Chimica Acta, 2004, pp. 73-81, vol. 87.
Gevrenoca, R. et al., Root in vitro cultures of six Gypsophila species and their saponin contents, Enzyme and Microbial Technology, May 18, 2020, pp. 97-104, vol. 47.
Haddad, M., Miyamoto, T., Ramezani, M. and Lacaille-Dubois, M.A., 2004. New triterpene saponins from Acanthophyllum pachystegium. Helvetica chimca acta, 87(1), pp. 73-81.
Gevrenova, R., Stancheva, T., Voynikov, Y., Laurain-Mattar, D. and Henry, M., 2010. Root in vitro cultures of six Gypsophila species and their saponin contents. Enzyme and microbial technology, 47(3), pp. 97-104.
Weng, A., Thakur, M., Von Malinckrodt, B., Beceren-Braun, F., Gilabert-Oriol, R., Wiesner, B., Eichhorst, J., Böttger, S., Melzig, M.F. and Fuchs, H., 2012. Saponins modulate the intracellular trafficking of protein toxins. Journal of controlled released, 164(1), pp. 74-85.
Yao, Shun & Ma, Li & Luo, Jian-Guang & Wang, Junsong & Kong, Ling-Yi. (2010). Triterpenoid Saponins from the Roots of Gypsophila paniculata. Chinese Journal of Natural Medicines. 8. 28-33, 10.3724/SP.J. 1009.2010.00028.

*Primary Examiner* — Layla D Berry
(74) *Attorney, Agent, or Firm* — N.V. Nederlandsch Octrooibureau

(57) ABSTRACT

The present invention relates to the novel use of saponins having acetyl residues on one of their sugar residues. These saponins are able to enhance the transfection efficiency to a surprisingly much higher extent than already known saponins and even than Lipofectamin.

11 Claims, 12 Drawing Sheets

USES OF A SAPONIN AND METHOD FOR ITS ISOLATION

The present invention relates to the in vitro use of a saponin according to the preamble of claim 1, to the in vivo use of such a saponin according to the preamble of claim 3, to a transfection composition according to the preamble of claim 7, to a method for an in vitro transfection according to the preamble of claim 10, and to a method for isolating such a saponin according to the preamble of claim 15.

Many saponins have been described in the past. Exemplarily, reference is made to Weng, Alexander, et al. "A simple method for isolation of *Gypsophila* saponins for the combined application of targeted toxins and saponins in tumor therapy." *Planta medica* 75 (13) (2009): 1421-1422; Weng, Alexander, et al. "A convenient method for saponin isolation in tumour therapy." *Journal of Chromatography B* 878 (7) (2010): 713-718; Weng, Alexander, et al. "The toxin component of targeted anti-tumor toxins determines their efficacy increase by saponins." *Molecular oncology* 6 (3) (2012): 323-332; and Weng, Alexander, et al. "Saponins modulate the intracellular trafficking of protein toxins." *Journal of controlled release* 164 (1) (2012): 74-86.

Further saponins are described in the following publications: Thakur, Mayank, et al. "High-speed countercurrent chromatographic recovery and off-line electrospray ionization mass spectrometry profiling of bisdesmodic saponins from *Saponaria officinalis* possessing synergistic toxicity enhancing properties on targeted antitumor toxins." *Journal of Chromatography B* 955 (2014): 1-9; Jia, Zhonghua, Kazuo Koike, and Tamotsu Nikaido. "Major triterpenoid saponins from *Saponaria officinalis*." *Journal of natural products* 61 (11) (1998): 1368-1373; Haddad, Mohamed, et al. "New triterpene saponins from *Acanthophyllum pachystegium*." *Helvetica chimica acta* 87 (1) (2004): 73-81; Fu, Hongzheng et al. "Silenorubicosides A-D, Triterpenoid Saponins from *Silene rubicunda*." *Journal of Natural Products* 68 (5) (2005): 754-758; Moniuszko-Szajwaj, Barbara, et al. "Highly Polar Triterpenoid Saponins from the Roots of *Saponaria officinalis* L." *Helvetica Chimica Acta* 99 (5) (2016): 347-354; Fuchs, Hendrik, et al. "Glycosylated Triterpenoids as Endosomal Escape Enhancers in Targeted Tumor Therapies." *Biomedicines* 5 (2) (2017): 14.

It has also been described that a specific saponin (SO1861) can mediate an improved intracellular delivery of peptide and lipid nanoparticles (Weng, Alexander, et al. "Improved intracellular delivery of peptide- and lipid-nanoplexes by natural glycosides." *Journal of Controlled Release* 206 (2015): 75-90).

It is an object of the present invention to provide a compound having even better properties with respect to intracellular delivery of small compounds such as peptides and nucleic acids than the saponin SO1861.

Surprisingly, a saponin that can be isolated from *Gypsophila elegans* M. Bieb has superior effects regarding the delivery of small molecules, in particular regarding the delivery of nucleic acids to cells. Such a saponin corresponds to formula (I):

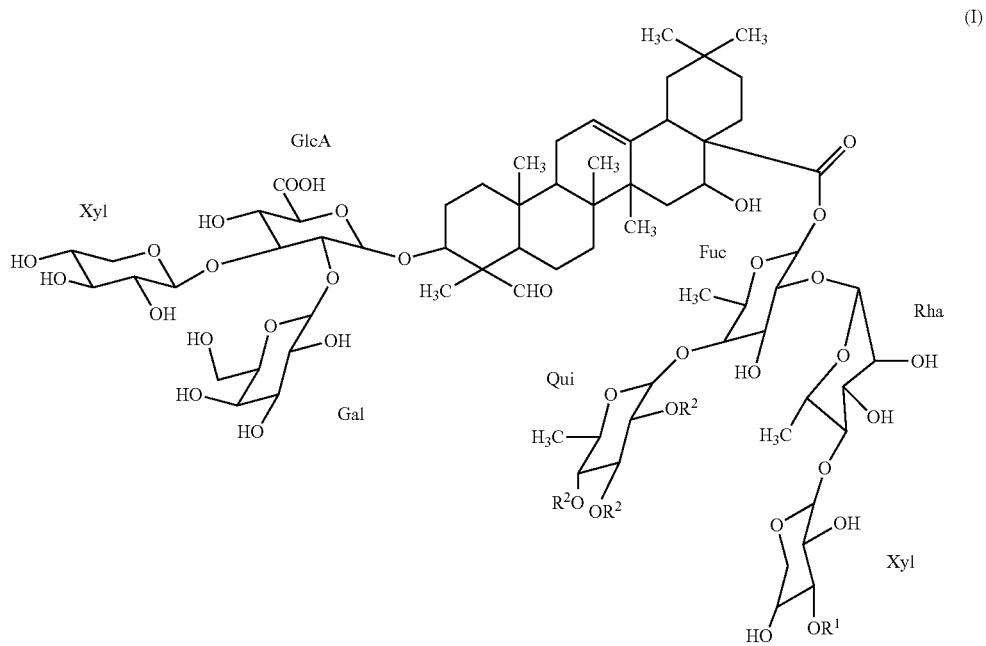

Thereby, $R^1$ is a xylose residue or an arabinose residue bonded with its C1 atom to the corresponding xylose residue of formula (I); and $R^2$ is independent from other $R^2$ residues in the same molecule H or an acetyl residue, with the proviso that at least two acetyl residues are present in the saponin.

The saponin has a common saponin core structure and does not comprise any unusual bonds. Rather, it differs from other saponins only in its sugar residues and/or its acetyl residues.

For a better identification of the individual sugar residues in formula (I), they are marked with a corresponding abbreviation in the above depiction of formula (I). Thereby, the abbreviations have the following meaning:

| Abbreviation | Sugar residue |
|---|---|
| Fuc | Fucose |
| Gal | Galactose |
| GlcA | Glucuronic acid |
| Qui | Quinovose |
| Rha | Rhamnose |
| Xyl | Xylose |

The structure of arabinose (Ara) corresponds to formula (II):

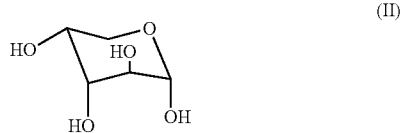

(II)

A compound according to formula (I) showed a transfection efficiency that was approximately twice as high as the transfection efficiency of SO1861. This is a completely unexpected and surprising result since one would expect only slight increases in transfection efficiency with respect to SO1861. Due to the high number of already existing saponins, the inventors could not expect that the compounds the use of which is claimed here would show such a high transfection efficiency even if these compounds are known per se. Saponins cannot be synthesized and can generally not simply be purchased from a supplier of chemicals. Rather, they need to be isolated from plants or parts of plants. This makes it particularly difficult to investigate the properties of saponins.

The inventors surprisingly found that saponins according to general formula (I) can be isolated from *Gypsophila elegans* M. Bieb that show an unexpected high transfection efficiency. It has not been described before that such saponins can be extracted from *Gypsophila elegans* M. Bieb. Rather it has only been described by Haddad et al. (see above for details) that a saponin falling under general formula (I) has been isolated from a completely different plant (Acanthophyllum pachystegium) without, however, giving any indication that this saponin could increase the transfection efficiency.

Thus, the present invention relates to the use of a saponin according to general formula (I) in the in-vitro delivery of a nucleic acid, a lipid, a peptide and/or a protein to a cell. Thereby, the in vitro delivery of nucleic acid is a particularly appropriate use of the saponin. Appropriate nucleic acids to be delivered are DNA, such as plasmid DNA or minicircle DNA, and RNA, such as small interfering RNA (siRNA). The nucleic acid or other molecule to be delivered can be present in the form of a nanoplex. Nanoplexes are typically formed by peptides or lipids being able to bind the small molecule to be delivered. Thus, a nucleic acid delivering nanoplex comprises a lipid or non-lipid carrier to which a nucleic acid is bound. Nanoplexes as can also be referred to as nanoparticles. In an embodiment, the nucleic acid to be delivered is a minicircle DNA. In an embodiment, the molecule to be delivered is a peptide minicircle DNA particle.

In an embodiment, the cell to which the nucleic acid, the lipid, the peptide and/or the protein is to be delivered is a eukaryotic cell. Human cells, animal cells (such as rodent cells) or plant cells are particularly appropriate to be used as cells. Yeast cells can also be used.

In an aspect, the invention relates to the use of a saponin according to general formula (I) in therapy or diagnostics. Thereby, the saponin is used for an in-vivo delivery of a nucleic acid, a lipid, a peptide and/or a protein to a human or animal.

In an embodiment, the animal is a mammal, in particular a rodent.

In an aspect, a mixture of at least two saponins, in particular of exactly two saponins is used, wherein residue $R^1$ denotes xylose in a first saponin and arabinose in a second saponin.

In an embodiment, all sugars are present in their D stereoisomeric form.

In an embodiment, $R^1$ is a xylose residue. Then, the saponin corresponds to the following formula (III):

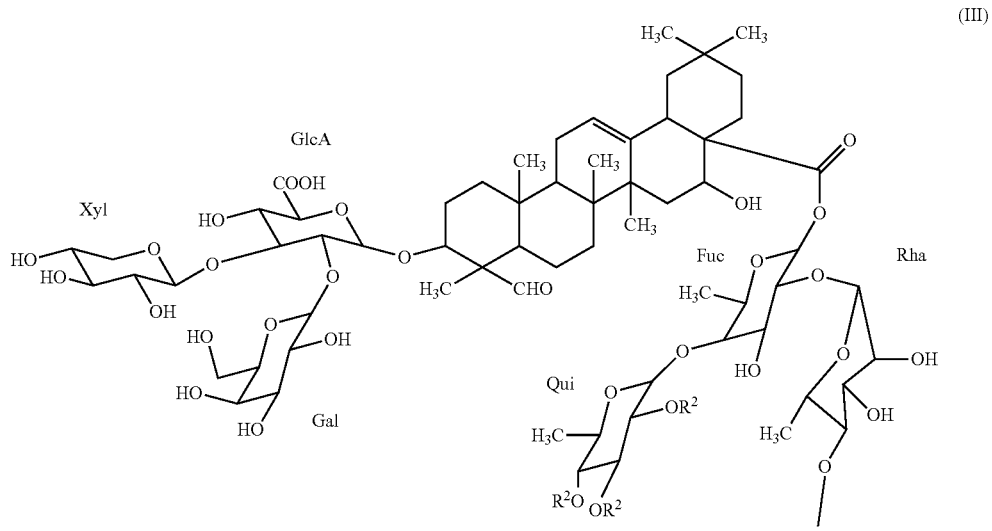

(III)

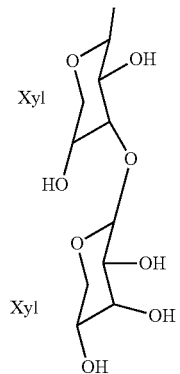
In an embodiment, $R^1$ is an arabinose residue. Then, the saponin corresponds to the following formula (IV):
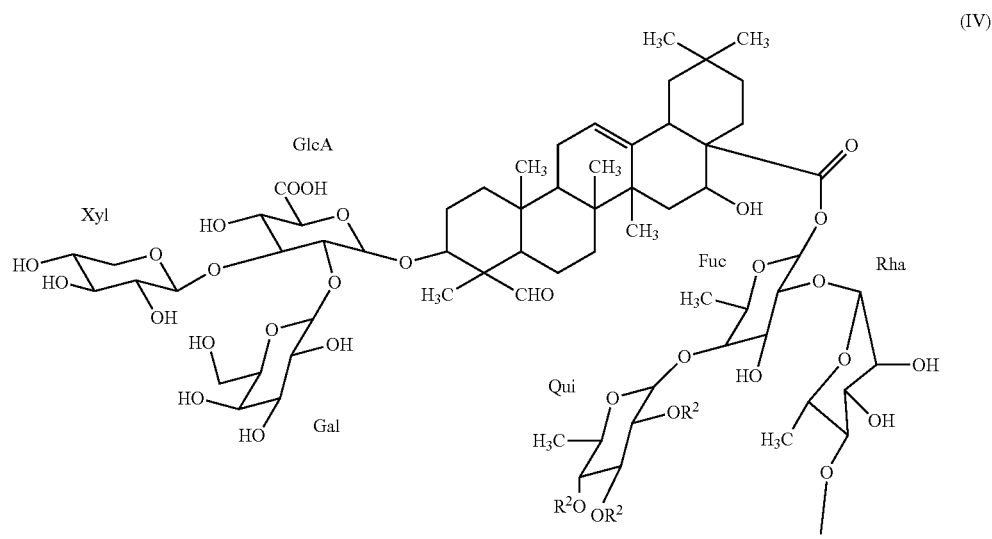
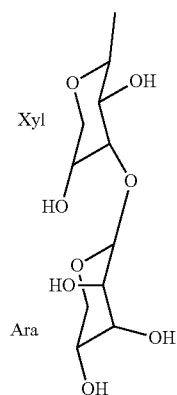

In an embodiment, the saponin is present in a stereoisomeric form according to general formula (V). Likewise, the xylose residue and the arabinose residue are present, in an embodiment, in a stereoisomeric form according to formulae (VI) or (VII):

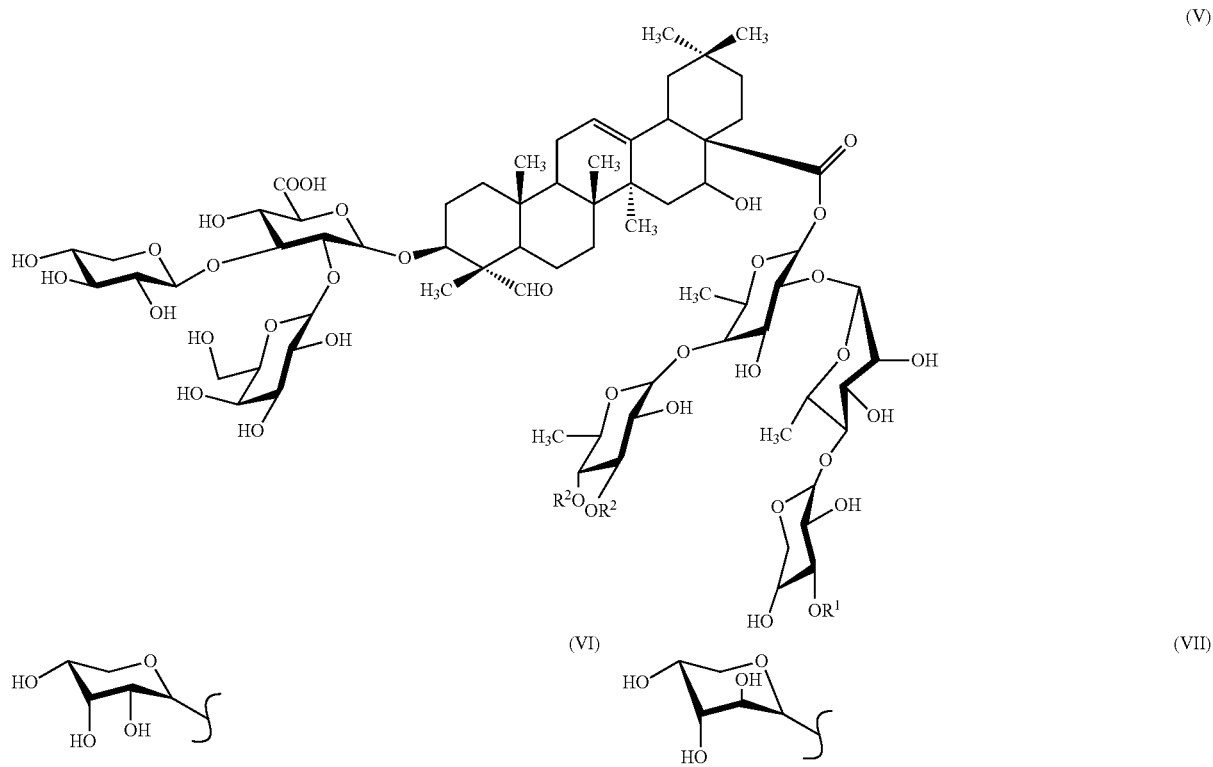

In an embodiment, the saponin carries exactly two acetyl groups, i.e., two of the $R^2$ residues are acetyl residues and the remaining $R^2$ residue is a hydrogen.

In an embodiment, the acetyl groups are bonded to the oxygen atoms in C3 and C4 position of the corresponding quinovose residue, resulting in a saponin of formula (VIII):

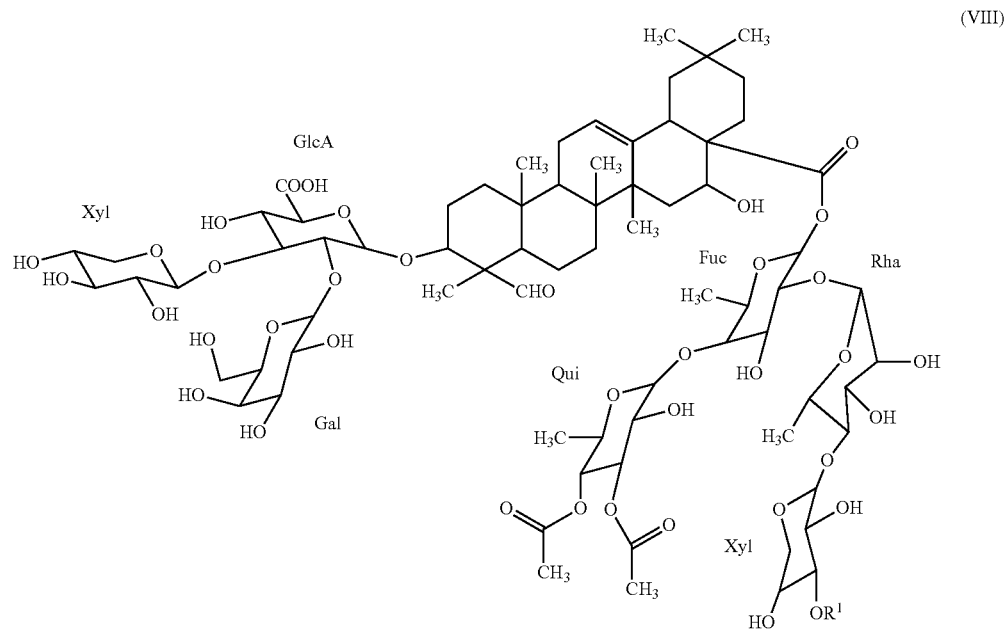

In an embodiment, all three $R^2$ residues are acetyl residues, resulting in a saponin of formula (IX):

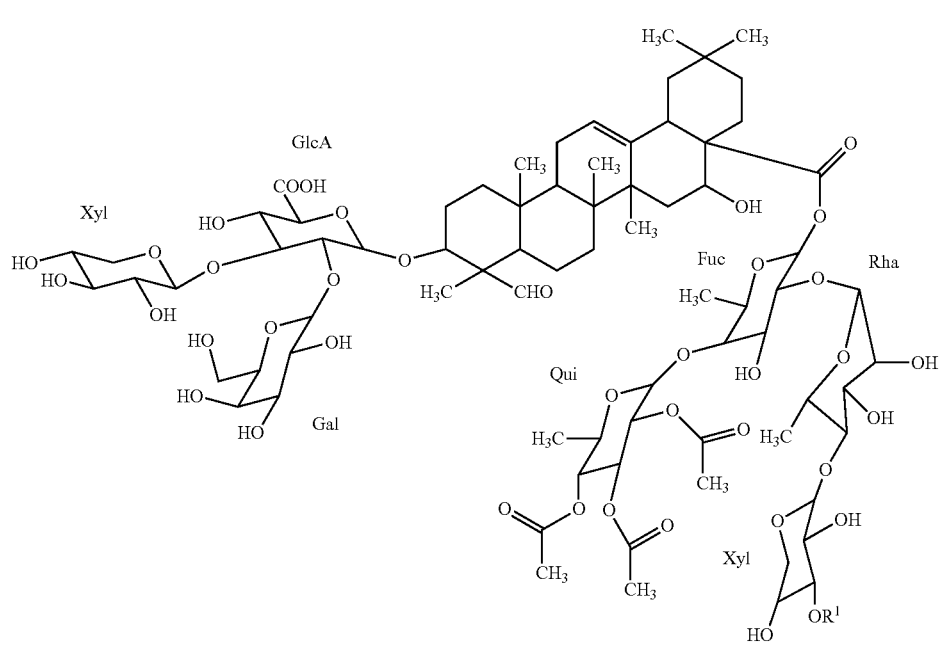

The inventors surprisingly found out that a saponin according to general formula (I) does not only increase the transfection efficiency when used alone, but is particularly appropriate to enhance the transfection efficiency of classic transfection reagents. Thus, it can be used as booster for such transfection reagents. The above-described uses encompass the use of such a saponin as booster for classic transfection reagents. In an embodiment, the saponin is used in vivo or in vitro in combination with at least one transfection reagent chosen from the group consisting of liposomal-based transfection reagents and polymer-based transfection reagent. Examples of such transfection reagents are listed below.

The general inventive concept between the independent claims is to be seen in the significant enhancement of transfection efficiency of the saponins according to general formula (I) that was uncovered by the inventors for the first time.

In an aspect, the invention relates to a transfection composition, comprising a classic transfection reagent and at least one saponin according to formula (I), wherein the residues $R^1$ and $R^2$ have the meanings described above. Classic transfection reagents can be divided into two subgroups, namely liposomal-based transfection reagents and polymer-based transfection reagents. Liposomal-based transfection reagents consist of mostly cationic charged lipids with hydrophobic fatty acid chains bound to polar head groups such as trimethylammonium propane. Polymer-based transfection reagents consist of organic polymers containing a charged head group such as polyethylenimine (PEI).

Examples for commercially available classic liposomal-based transfection reagents are METAFECTENE; Trans-Fast; Stemfect; and TransFectin.

Examples for commercially available classic polymer-based transfection reagents are GeneCellin; X-tremeGene transfection reagents such as X-tremeGene 9 DNA Transfection Reagent, X-tremeGene HP DNA Transfection Reagent, and X-tremeGene siRNA Transfection Reagent; TransIT transfection reagents such as TransIT-X2 Dynamic Delivery System, TransIT-LT1 Reagent, TransIT-2020 Reagent, TransIT-PRO Reagent, TransIT-VirusGEN Reagent, TransIT-*Lenti* Reagent, TransIT-Insect Reagent, TransIT-293 Reagent, TransIT-BrCa Reagent, TransIT-CHO Transfection Reagent, TransIT-HeLaMONSTER Transfection Reagent, TransIT-Jurkat Reagent, TransIT-Keratinocyte Reagent, TransIT-m RNA Transfection Reagent, TransIT-TKO Reagent, TransIT-siQUEST Reagent, and TransIT-Oligo Reagent; Viafect; FuGENE; Xfect; TurboFect; and GenJet.

In an embodiment, $R^1$ of the saponin in the transfection composition is a xylose residue.

In an embodiment, the saponin in the transfection composition carries exactly two acetyl groups.

In an embodiment, the acetyl groups are bonded to the oxygen atoms in C3 and C4 position of the corresponding quinovose residue.

In an embodiment, the transfection reagent is a liposomal-based transfection reagent.

In an embodiment, the transfection reagent is a polymer-based transfection reagent.

In an embodiment, the transfection reagent is chosen from the group consisting of a TransIT transfection reagents, X-tremeGene transfection reagents, and GeneCellin.

In an embodiment, the transfection reagent is GeneCellin.

In an aspect, the invention relates to method for delivering a nucleic acid, a lipid, a peptide and/or a protein to a human or animal in need thereof by using a saponin or a mixture of at least two saponins according to the preceding explanations.

In an aspect, the invention relates to a method for an in vitro transfection of a cell. This method comprises the step of incubating a cell with a nucleic acid in the presence of a saponin or a mixture of at least two saponins according to the preceding explanations. The transfection can be a transient transfection or a stable transfection. DNA and RNA are appropriate nucleic acids, wherein DNA is particularly appropriate. In an embodiment, the nucleic acid to be delivered is a minicircle DNA.

In an embodiment, the cell is a eukaryotic cell. Human cells, animal cells (such as rodent cells) or plant cells are particularly appropriate to be used as cells. Yeast cells can also be used.

In an embodiment, the nucleic acid forms part of a nanoparticle. To give an example, a DNA nanoparticle may be used. Peptide minicircle DNA particles or particles comprising a peptide bound to DNA are further appropriate examples. Likewise, RNA nanoparticles are appropriate entities to carry out the transfection.

In an embodiment, the saponin is used in a concentration lying in a range between 1 µg/mL and 25 µg/mL, in particular between 1.5 µg/mL and 20 µg/mL, in particular between 2 µg/mL and 15 µg/mL, in particular between 2.5 µg/mL and 12.5 µg/mL, in particular between 3 µg/mL and 10 µg/mL, in particular between 4 µg/mL and 9 µg/mL, in particular between 5 µg/mL and 8 µg/mL, in particular between 6 µg/mL and 7 µg/mL.

In an embodiment, the saponin is used within the claimed method in combination with at least one transfection reagent chosen from the group consisting of liposomal-based transfection reagents and polymer-based transfection reagent. Examples of such transfection reagents are listed above.

In an aspect, the present invention relates to method for isolating a saponin or a mixture of at least two saponins according to the preceding explanations from *Gypsophila elegans* M. Bieb. This method comprises the steps explained in the following. Thereby, the steps need not necessarily be performed in the indicated order. Rather, any other sensible order of method steps can also be applied.

In a first step, roots of *Gypsophila elegans* M. Bieb are cut. Optionally, the cut roots are washed. Subsequently, the cut roots are freeze-dried and ground. In doing so, a root powder is obtained.

The root powder is extracted with a high-concentrated organic solvent to obtain a root extract. The term "high-concentrated organic solvent" relates to an organic solvent having a concentration of more than 50% (v/v). Methanol or any other short-chain organic alcohol is a suited organic solvent. To give an example, a solvent concentration of 70 to 100%, in particular of 75 to 95%, in particular of 80 to 90% is an appropriate high concentration. If the organic solvent is miscible with water, water can be used as co-solvent.

Afterwards, the high-concentrated organic solvent is removed from the root extracts to obtain a dry extract. This removal can be performed, e.g., by vacuum distillation.

The dry extract is then dissolved in a low-concentrated organic solvent to obtain an extract solution. The term "low-concentrated organic solvent" relates to an organic solvent having a concentration of less than 50% (v/v). To give an example, a concentration of 10% to 50%, in particular of 15% to 45%, in particular of 20% to 40%, in particular of 25% to 30% is an appropriate concentration range for the low-concentrated organic solvent. Once again, methanol or any other short-chain organic alcohol is a suited organic solvent. Likewise, water can be used as co-solvent, if the low concentrated organic solvent is miscible with water.

The extract solution is then subjected to at least one chromatographic separation step. Thereby, a purified saponin solution is obtained. The chromatographic separation can be implemented by high-performance liquid chromatography (HPLC). Typically, it is advisable to perform more than one chromatographic separation step in order to enhance the purity of the purified saponin solution. Thus, it is possible to subject the purified saponin solution obtained after the first chromatographic separation step to at least one subsequent chromatographic separation step. Thereby, different columns can be used in the individual chromatographic separation steps.

It is possible to perform the individual chromatographic separation steps (if more than one chromatographic separation step is carried out) in different stationary and/or mobile phases. Thus, it is possible to change the solvents used in the individual chromatographic separation steps between these steps.

Finally, the solvent is removed from the purified saponin solution after the at least one chromatographic separation step. This can, e.g., be done by vacuum distillation or by freeze-drying. A purified saponin powder results.

All embodiments disclosed herein can be combined in any desired way. Furthermore, embodiments of the explained uses and methods can be transferred to the described other methods and uses in any desired way. The described transfection composition can also make use of any of the described embodiments.

Further details of aspects of the present invention will be explained with respect to an exemplary embodiment and accompanying Figures. In the Figures.

EXEMPLARY EMBODIMENT: ISOLATION OF THE SAPONIN GE1741 FROM *GYPOSPHILA ELEGANS* M. BIEB

Seeds from *Gypsophila elegans* M. Bieb were seeded on a field in the state of Brandenburg, Germany. The mature plants were harvested and the roots were cut. The roots were washed, freeze-dried and ground to powder. The powder was extracted by 90% methanol in water. Following filtration, the methanol was removed by vacuum distillation. The remaining aqueous extract was finally freeze-dried (dry extract). The dry extract was dissolved in 30% methanol at a concentration of 60 mg/mL.

Figure 1:
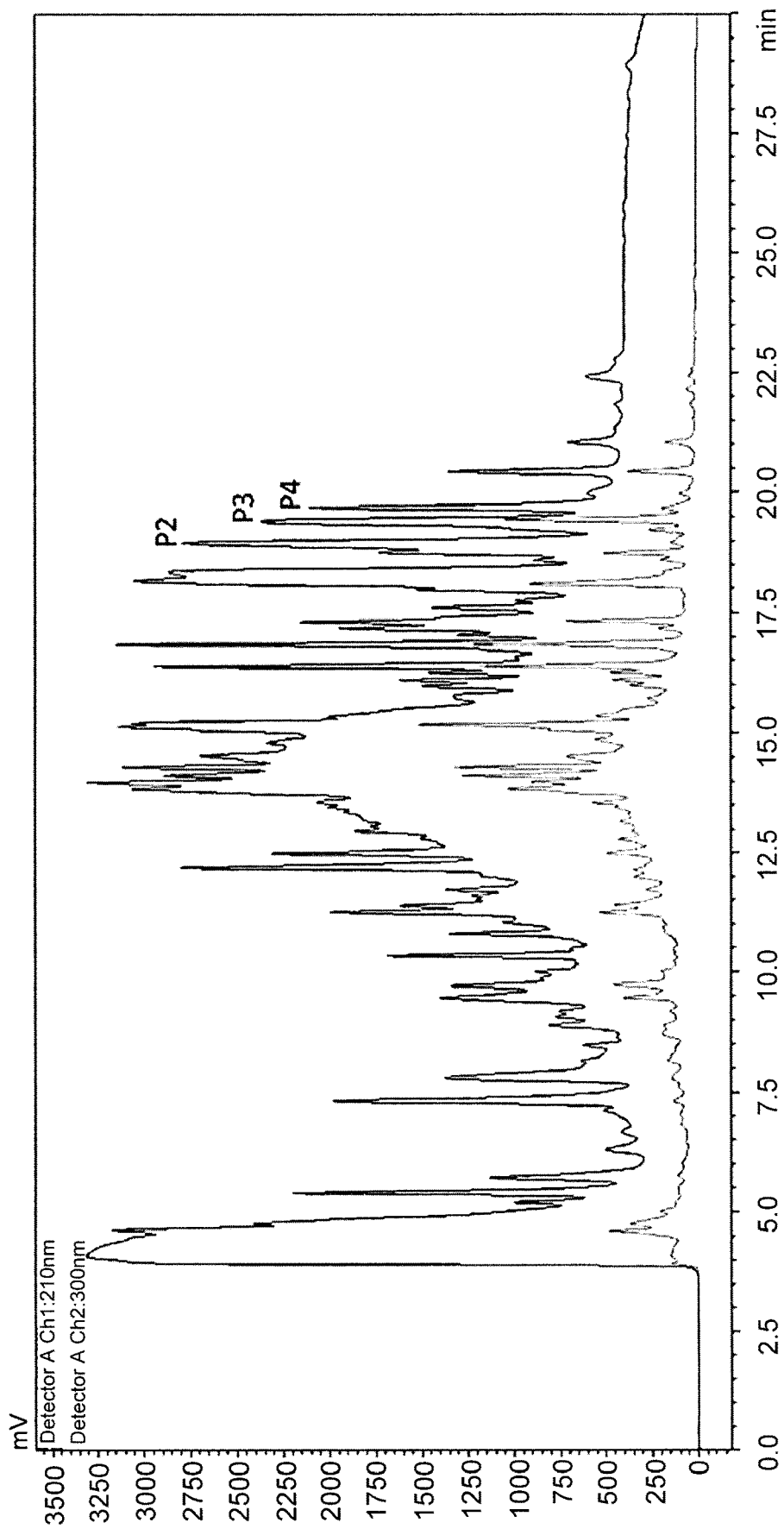
FIG. 1 shows an HPLC chromatogram of dry raw extract from the roots of *Gypsophila elegans* M. Bieb.

The solution (each 0.5 mL) was subjected to semi-preparative HPLC using a Kinetex® 5 µm C18 100 Å, LC Column 250×10.0 mm. A methanol(A)/water, 0.01% TFA (B) gradient was used from 30% to 90% (A) over 20 min and then to 30% (A) over 10 min. Flow rate was 4 mL/min. Detection wavelength was at 210 and 300 nm. A corresponding chromatogram is depicted in FIG. 1, wherein the upper curve shows the detector signal at 210 nm and the lower curve the detector signal at 300 nm. The peak at a retention time (RT)≈18 to 20 (≈19) min (marked as P2) was collected. A high number of isolation cycles was repeated and the collected peaks were finally pooled. The methanol was evaporated by vacuum centrifugation and the remaining water was removed by freeze-drying.

The dried material was dissolved in 50% acetonitrile at a concentration of 4 mg/mL. The solution (each 0.5 mL) was subjected to semi-preparative HPLC using a Kinetex® 5 µm C18 100 Å, LC Column 250×10.0 mm. An acetonitrile (A)/water, 0.01% TFA (B) gradient was used from 30% to 50% (A) over 24 min and then to 30% (A) over 1 min. Detection wavelength was at 210 nm. Flow rate was 4 mL/min. The peak at RT≈18 min was collected. Several cycles were repeated. The acetonitrile was evaporated by vacuum centrifugation and the remaining water was removed by freeze-drying.

Figure 2:
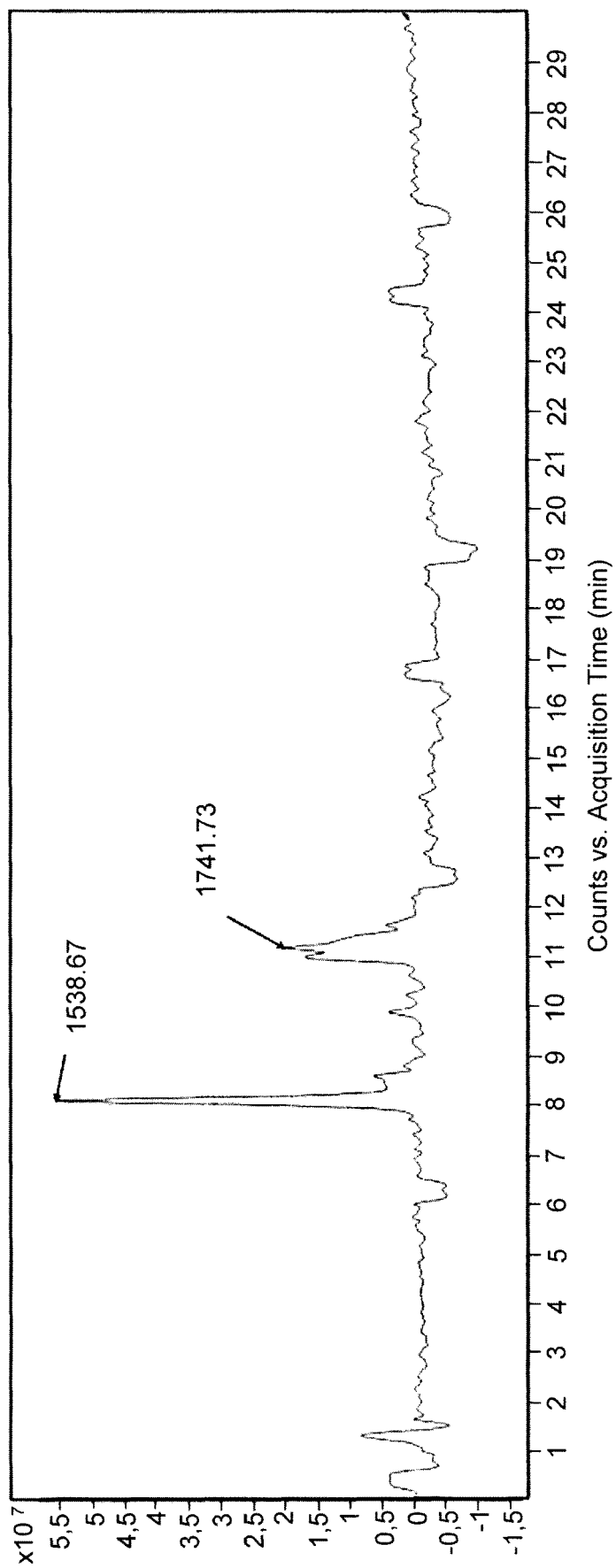
FIG. 2 shows an LC-ESI-MS chromatogram of the substance present in peak P2 of the chromatogram of FIG. 1 after further purification by semi-preparative HPLC.

The samples were analyzed by using an Agilent 6200 Series Q-TOF LC-ESI-MS/MS system. For LC-ESI-MS analysis of the recovered fractions a Kinetex® C18 HPLC column (2.6 µm, 100 Å, (150×4.6 mm), and acetonitrile (A)/water (B) gradient, 0.01% formic acid was used starting with 30% to 70% (A) over 30 min using a flow rate of 0.7 mL/min. The corresponding chromatogram is depicted in FIG. 2. Two prominent peaks were detected. A mass of 1538.67 was assigned to the substance of the first peak, and a mass of 1741.73 was assigned to the substance of the second peak. The second peak was chosen for further purification.

The dried material of the second peak was dissolved in 50% acetonitrile at a concentration of 4 mg/mL. The solution (each 0.5 mL) was subjected to semi-preparative HPLC using the semi-preparative Kinetex® C-18 column (see above). An acetonitrile (A)/water, 0.01% TFA (B) gradient was used from 30% to 50% (A) over 24 min and then to 30% (A) over 1 min using a flow rate of 4.0 mL/min. Detection wavelength was at 210 nm. The peak at RT≈18 min was collected in several repeating cycles. The acetonitrile was evaporated by vacuum centrifugation and the remaining water was removed by freeze-drying.

The dry material was dissolved in 50% acetonitrile and subjected (0.5 mL per run) to HPLC using an Ultrasep ES PEO, LC Column, 250×4 mm, 5 µm. The column was conditioned by 5% acetonitrile. The polarity of the solvent was abruptly changed by applying an acetonitrile(A)/water, 0.01% TFA (B) gradient starting with 100% to 5% (A) from 1.25 to 21 min. Detection wavelength was at 210 nm and flow rate was 1 ml/min. The product (GE1741; also referred to as gypsophilosid A) was collected at RT 4-6 min. The acetonitrile was removed by vacuum centrifugation. After freeze drying GE1741 was obtained as white powder.

Figure 3:
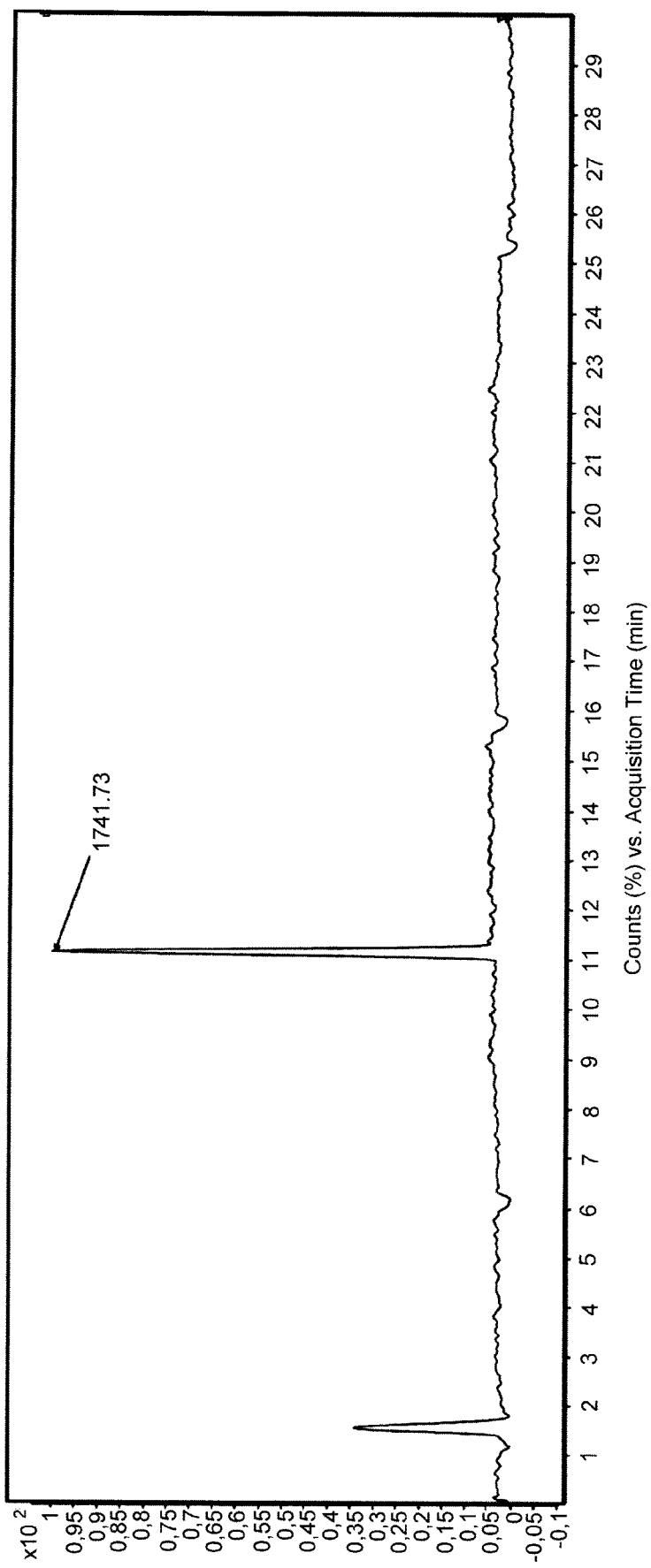
FIG. 3 shows and LC-ESI-MS chromatogram of the isolated saponin GE1741.

The product was once again analyzed by LC-ESI-MS as outlined above. The corresponding chromatogram is depicted in FIG. 3. Only one prominent peak was detected, indicating a successful purification. A mass of 1741.73 was assigned to the substance of this peak. This mass gave the product its name, GE1741.

Figure 4:
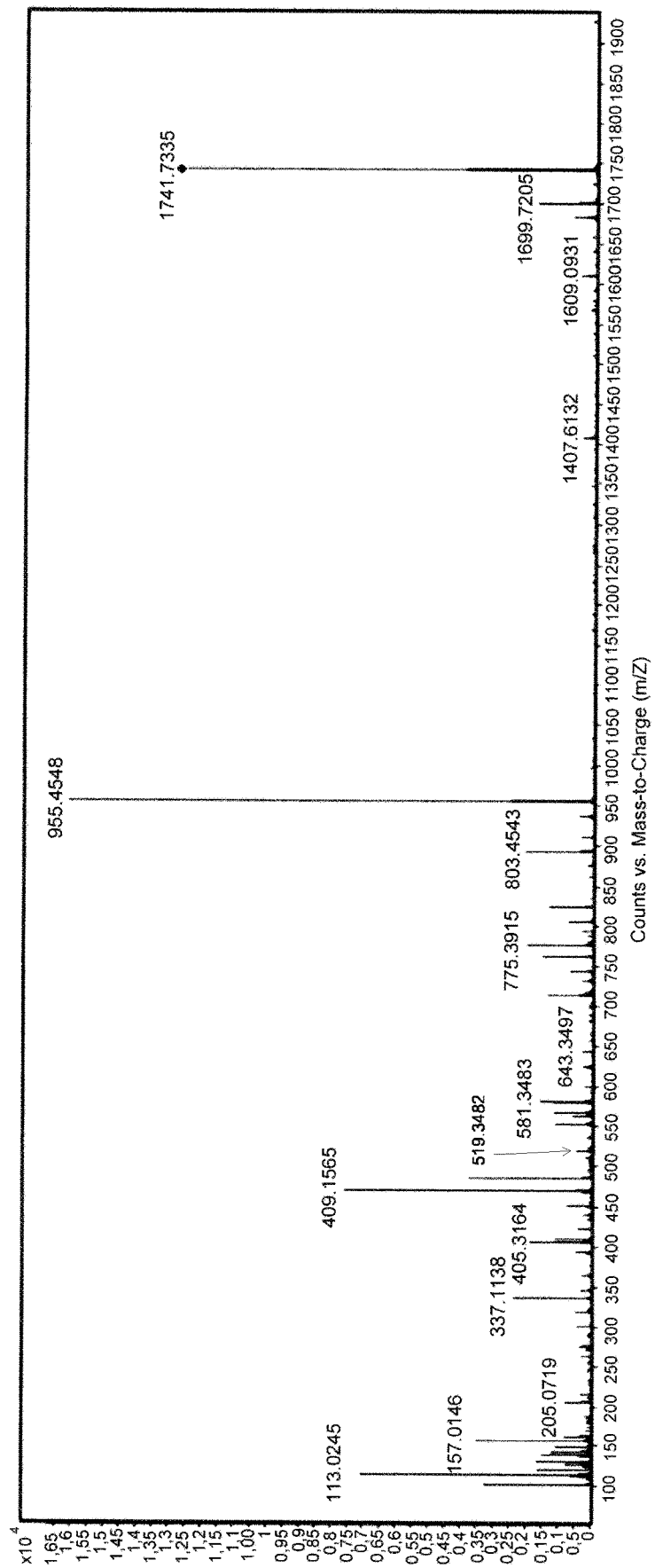
FIG. 4 shows an MS/MS spectrum of the isolated saponin GE1741.

For elucidating the chemical structure of GE1471, LC-ESI-MS/MS measurements were performed. A corresponding spectrum is shown in FIG. 4.

Based on this mass spectrometric data and further data obtained by NMR spectroscopy (see below for details), it could be established that the structure of this saponin corresponds to formula (VIII), wherein $R^1$ is a xylose residue. However, it is assumed that the biological function of GE1741 will most probably not depend on the concrete structure of residue $R^1$. Rather, the presence of at least one acetyl residue on the quinovose residue of GE1741 is considered to be a relevant factor for the properties of GE1741 that will be explained in the following in more detail. While GE1741 comprises two acetyl residues (one in C3 position and one in C4 position), preliminary data suggests that the amount and position of the acetyl residues can be varied within the indicated limits without significantly changing the properties of the respective saponin.

Testing the Properties of GE1741
Cell Culture

Murine neuroblastoma cells (Neuro2a cells, ATTC CCL-131™) and human colorectal carcinoma cells (HTC-116, (ATCC® CCL-247™) were cultured in Dulbecco's Modified Eagle's Medium (DMEM), containing 1 g/L D-Glucose, 10% FBS and stable glutamine. Neuro-2A-cells were incubated at 37° C. and 5% $CO_2$. These cells were then incubated with DNA nanoparticles (YD) with or without the novel saponin GE1741.

The DNA nanoparticles used for the transfection experiments contained DNA encoding for the green fluorescent protein (GFP). Therewith, the transfection efficiency could very easily be monitored by detecting the fluorescence of the cells that have been incubated with the corresponding DNA nanoparticles. The corresponding incubation period was chosen to be 48 hours in the present case.

As negative control (left panel of FIG. 5), no DNA nanoparticles at all have been added to the Neuro2a cells. A fluorescence indicating an apparent transfection efficiency of 0.37% could be observed. This value represents the measuring error.

Figure 5:
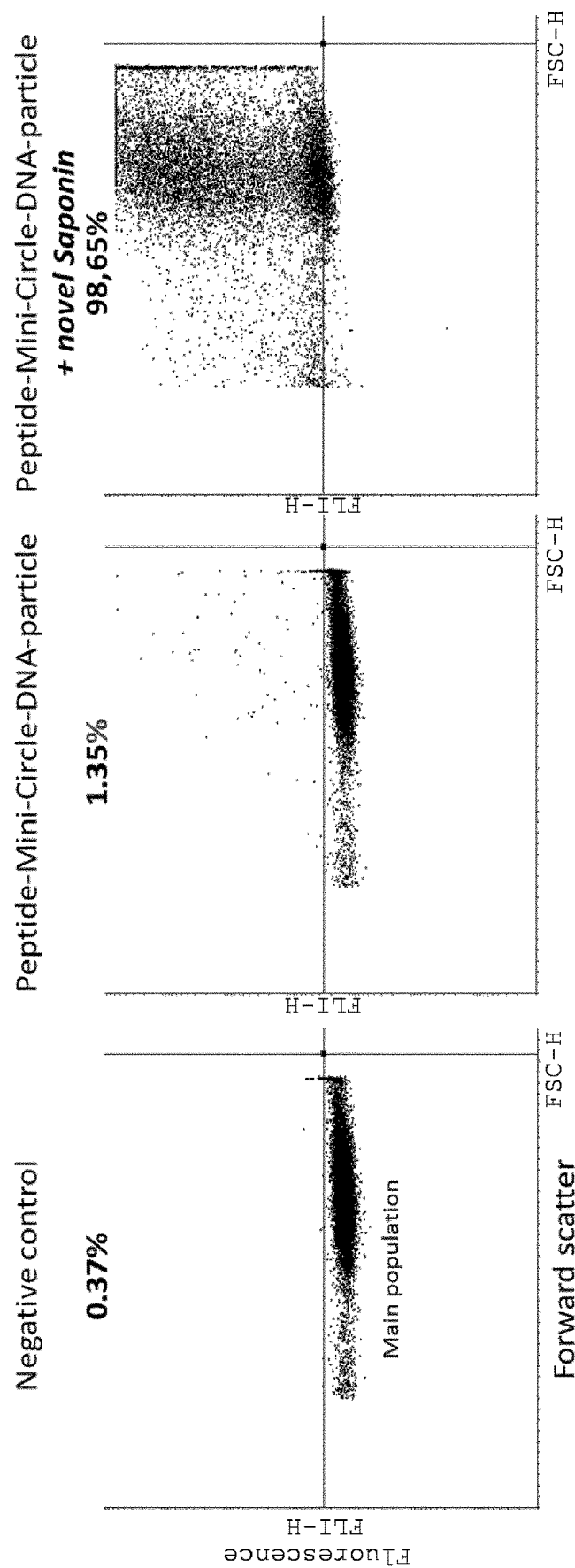
FIG. 5 shows the results of flow cytometric measurements.

If peptide minicircle DNA particles (PM) have been added to the Neuro2a cells without any transfection enhancer, a transfection efficiency of only 1.35% could be observed based on the detected fluorescence (middle panel of FIG. 5). If, however, the same peptide minicircle DNA particles have been added together with GE1741 (the novel saponin), a transfection efficiency of 98.65% could be observed based on the detected fluorescence (right panel of FIG. 5). These flow cytometric measurements detecting fluorescent cells already indicates a high transfection efficiency enhancement by GE1741.

Formulation of PD/YD—Nanoplexes 20 mg of positively charged poly-lysine peptides with (Y) and without (P) an integrin receptor targeting amino sequence were purchased from Genecust. The vector of p-EGFP-N3, coding for the green fluorescing protein (GFP), was obtained and propagated with DH5α—*E. Coli* cells (1.645 mg/mL). StemMACS™ eGFP mRNA (20 µg) and GFP encoding minicircle DNA (Gene Bank Accession: U55761) were used as further nucleic acids. In order to conduct the transfection, nanoplexes were formulated as follows: The poly-lysine peptides (P or Y) and the p-EGFP-N3 (D), mRNA (m) or minicircle (M) vector were diluted in water (each 50 µL) and mixed thoroughly by fast pipetting in a ratio of 4:1. The nanoplexes were allowed to form in a 30-minute incubation step. Thereafter, the nanoplex suspension was diluted with OptiMEM to a total volume of 1 mL. The commercial transfection reagents TransIT-X2® Dynamic Delivery System, Xtreme GENET™ HP Transfection Reagent, Genecellin and Lipofectamin® were formulated as described by the manufacturer.

Sapofection (Transfection with Triterpene Saponins)

Neuro2a cells or HTC-116 cells (15,000 cells/well) were seeded in a 24-well-plate with a well volume of 400 μL culture medium and incubated for 24 h. The transfection reagents were formulated as described above and admixed with saponin solution, if required. The culture medium was replaced with the transfection medium with a final amount of 500 ng DNA/RNA. After a 48 h (DNA transfections) or 24 h (RNA transfections) incubation period, the transfection medium was removed, the cells were trypsinized and transferred in a polystyrene tube for flow cytometry (Cytoflex). For each measurement 10,000 cells were acquired. The transfection efficiency was determined by the analysis software Cyflogic (by comparison of the sample plots with the negative control in terms of fluorescence.

Cell Impedance Measurements

For real-time toxicity measurements the impedance measuring device iCELLigence® was deployed. 8000 Neuro2a cells per well were seeded into two 8-well E-plates L8 and incubated for 24 h in a volume of 800 μL. For transfection toxicity studies 50 μL of reagent was added after the respective volume of culture medium was removed. A non-toxic concentration of 2 μg/mL GE1741 was applied. For permeability studies increasing concentrations of GE1741 from 2.5 μg/mL to 60 μg/mL were applied to the cells. Each 10 minutes the impedance/viability was measured. The results were analyzed and displayed with the RTCA Data Analysis Software.

NMR Spectroscopy

The samples for NMR-spectroscopy were prepared by dissolving 2 mg of GE 1741 in 600 μl $d_4$-methanol (99.95% deuterium content, Deutero, Kastellaun, Germany) and by dissolving 4 mg of GE 1741 in 600 μl $d_5$-pyridine (99.9% deuterium content, Deutero, Kastellaun, Germany) to yield a concentration of 1.9 and 3.8 mM/l, respectively. The solutions were transferred to 5 mm sample tubes which were sealed to prevent evaporation of solvent or accumulation of water.

NMR spectra were recorded at 300 K at 600 ($^1$H frequency) on Bruker AV-III spectrometers (Bruker Biospin, Rheinstetten, Germany) using cryogenically cooled 5 mm TCI-triple resonance probe equipped with one-axis self-shielded gradients. The software used to control the spectrometer was topspin 3.5 pl6. Temperature had been calibrated using do-methanol and the formula of Findeisen et al. (Findeisen 2007).

Experiments using the sample in methanol: One-dimensional $^1$H- and $^{13}$C-spectra were recorded at 600 MHz using 32 and 18432 scans, respectively. In case of the carbon spectrum proton broadband decoupling was applied. Homonuclear spectra: A DQF-COSY (Piantini et al., 1982), a TOCSY (Braunschweiler and Ernst, 1983; Bax and Davis, 1985a) and a NOESY (Jeener et al., 1979) were recorded using 2048×512 complex data points and acquisition times of 204 and 61 ms in F2 and F1, respectively. DQF-COSY and TOCSY (mixing time 80 ms) were recorded using 8 scans, the NOESY using 64 scans with a mixing time of 80 msec. The heteronuclear spectra were recorded as follows: A $^{13}$C-HSQC (Bodenhausen and Ruben, 1980), $^{13}$C-HSQC-TOCSY, $^{13}$C-HSQC-CLIP-COSY and $^{13}$C-HSQC-NOESY were recorded using 512×1024 complex data points, acquisition times of 51 and 45 ms in F2 and F1, respectively, and 48, 96, 96 and 288 scans, respectively. A $^{13}$C DEPT-HMQC (Kessler et al., 1989), and a $^{13}$C-HQQC (Kessler et al., 1991) were recorded using 512×512 complex data points, acquisition times of 51 and 23 ms in F2 and F1, respectively, and 64 and 60 scans, respectively. For the determination of the $^1$J HC and the $^3$J HH a $^{13}$C-HSQC was recorded without refocussing and carbon decoupling using 16384×512 complex data points, acquisition times of 1638 and 73 ms in F2 and F1, respectively, and using 32 scans. All the above heteronuclear spectra were recorded using a BIRD pulse for suppression of protons bound to $^{12}$C (Bax and Subramanian, 1986). A gradient-enhanced $^{13}$C-HMBC (Bax and Summers, 1986; Cicero et al., 2001) was recorded using 2048×1024 complex data points, acquisition times of 204 and 33 m sin F2 and F1, respectively, and 128 scans.

Experiments using the sample in pyridine: One-dimensional $^1$H- and $^{13}$C-spectra were recorded at 600 MHz using 32 and 14349 scans, respectively. In case of the carbon spectrum proton broadband decoupling was applied. A DQF-COSY (Piantini et al., 1982), was recorded using 2048×512 complex data points, 8 scans and an acquisition times of 204 and 61 ms in F2 and F1, respectively. A $^{13}$C-HSQC (Bodenhausen and Ruben, 1980), was recorded using 512×1024 complex data points, 32 scans and an acquisition times of 51 and 45 ms in F2 and F1, respectively. A gradient-enhanced $^{13}$C-HMBC (Bax and Summers, 1986; Cicero et al., 2001) was recorded using 2048×1024 complex data points, acquisition times of 204 and 33 ms in F2 and F1, respectively, and 64 scans.

Data were processed using topspin3.2, typically a squared sine bell shifted by 90° was used in both dimensions, in case of the HMBC a sine bell was used in F2. Datasets were processed to yield a data matrix of 4096 by 2048 points.

Isolation and Characterization of GE1741

Figure 6:
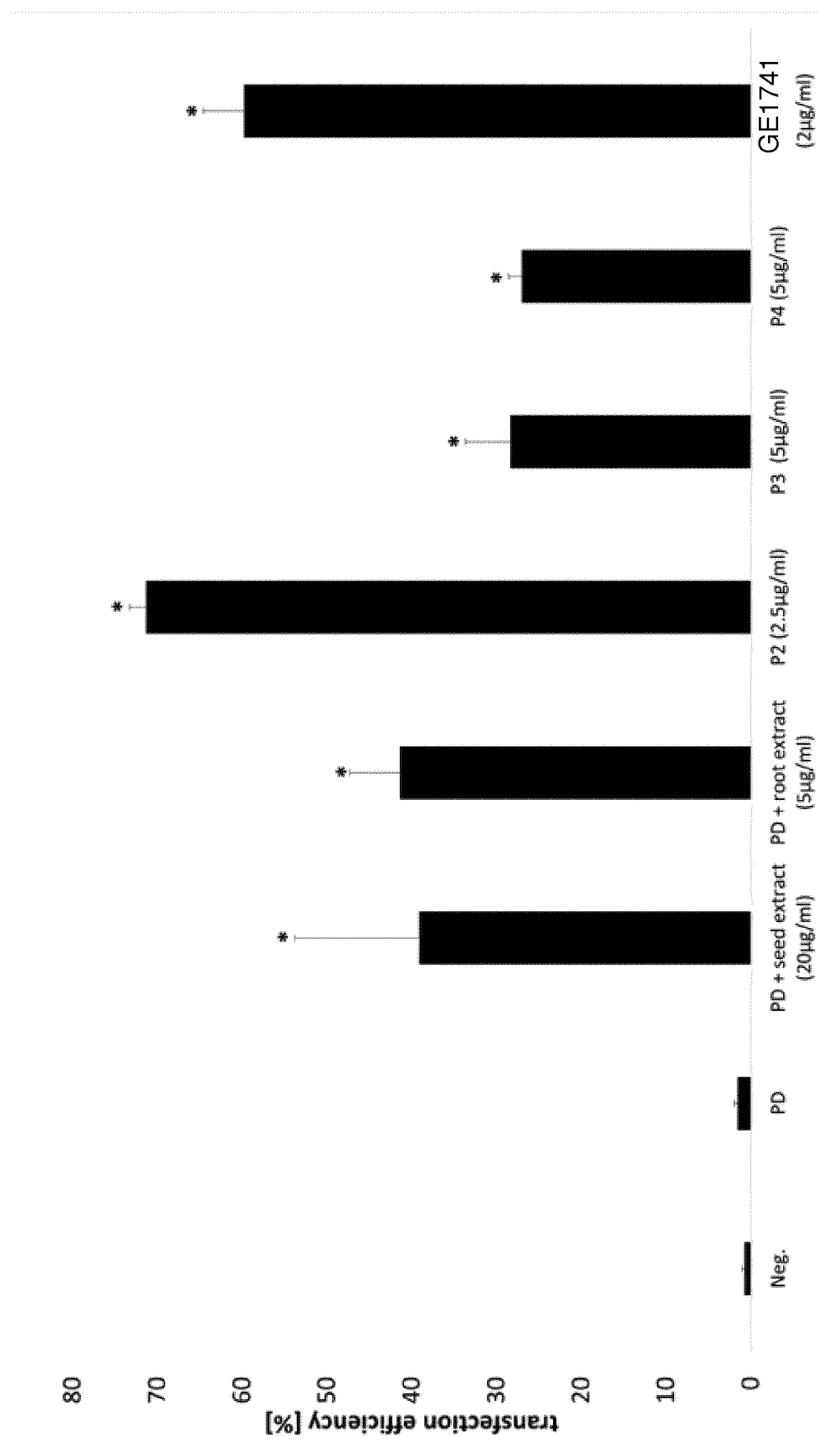
FIG. 6 shows the transfection efficiency of nanoplexes±triterpene saponins in Neuro2a cells.

Initially the seed and root extract was tested regarding transfection enhancing activity. The results are shown in FIG. 6. The HPLC chromatogram of the dry root extract (cf. FIG. 1) was analyzed, the peaks P2, P3 and P4 were collected and their biological activity was tested for their biological activity. These results are also shown in FIG. 6. Subsequently, P2 was subjected to further HPLC purification, as explained above. Subsequent LC-ESI-MS guided semi-preparative purification steps (cf. FIGS. 2 and 3) led to an isolation of a peak, which activity was repeatedly tested. LC-ESI-MS/MS measurements detected in the negative ionization mode the deprotonated molecular ion signal [M-H]—at m/z 1741 (cf. FIG. 4). The MS/MS fragment ion signal at m/z 955 was assigned to the saponin after secession of the di-acetyl-pentasaccharide chain linked to C-28 of the quillaic acid, and m/z 460 resulted after the additional cleavage of the trisaccharide unit at C-3. The molecular formula was determined to be $C_{79}H_{122}O_{42}$ (calculated: 1741.73325) from the measured mass for the negatively charged ion (HR-ESI-MS m/z 1741.7336). This corresponds to a mass difference of only 0.2 ppm.

1D- and 2D-NMR Spectroscopy of GE1741

The structure of the bidesmosic quillaic acid type saponin GE1741 was fully elucidated by 1D and 2D-NMR spectroscopic experiments, including $^1$H, $^{13}$C and HSQC, HMBC, HQQC, DQF-COSY, TOCSY, HSQC-TOCSY and NOESY using d4-methanol. Amongst the signals in the $^{13}$C NMR spectrum of GE174, two double intensity resonances (δC 75.33, 71.43 ppm) indicated completely overlapping of C-atoms. As partial structural units, a triterpene moiety and the existence of 8 sugars with two points of acetylation was seen. Using HSQC and HQQC experiments, six sp3-hybridised resonances (δC 10.9, 16.4, 17.7, 24.8, 27.1, 33.3 ppm) were recognized as methyl groups in the triterpene moiety, and additionally three methyl groups were assigned to deoxy-sugars (δC 17.0, 17.6, 18.3). The $^1$H NMR gave singlet resonances (δH 0.74, 0.87, 0.94, 1.00, 1.16, 1.38 ppm) for the triterpene methyl-functions, and doublets (δH 1.16, 1.23, 1.31) for the deoxy-functions.

Figure 7:
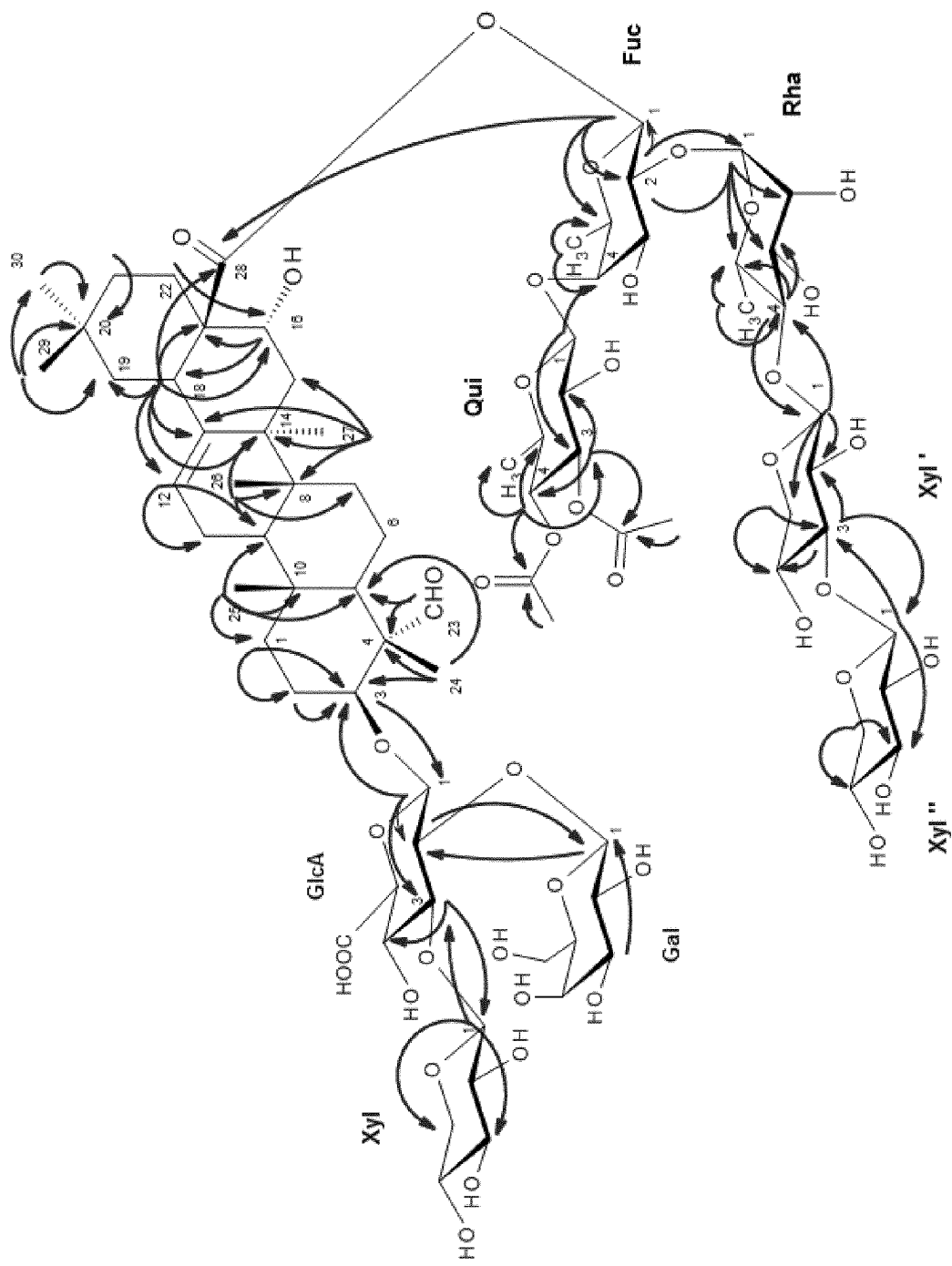
FIG. 7 shows the chemical structure of GE1741 elucidated by mass spectrometry and NMR spectroscopy.

The C30 corpus displayed two methyl groups less than expected which was explained by the occurrence of an aldehyde function (δC 211.5 ppm, δH 9.47 ppm) and an acidic function (δC 175.9 ppm). Together with resonances for a double bond at δC 123.2 (CH), 144.8 ppm (quaternary C), a broad triplet signal (δH 5.31 ppm), a substituted oxymethin function at C-3 (δC 86.4, δH dd 3.86) combined with HMBC correlation data elucidated a hydroxy-oleanan-12-ene type backbone. The corresponding results are shown in FIG. 7 and will be explained in more detail in the following
$^{2,3}$J CH correlations from the aldehyde proton δ 9.47 ppm to C-4 (56.3 ppm), CH3-24 (δ 10.9), and C-5. The long-range correlation of H-3 (δ 3.86) to the quaternary position C-4 and C-24 suggested the CHO-function to be at C-23. The second hydroxylation at C-16 (δC 74.5) was seen by $^{2,3}$J-CH signals from protons of H-18 (δ 2.94), CH2-22 (δ 1.93, 1.16). A total number of eight monosaccharides were detected in the structure of GE1741 by $^1$H- and $^{13}$C NMR spectroscopy by observation of characteristic chemical shifts of anomer resonances. The nomenclature of GE1741 is as follows: 3-O-(ß-D-Galactopyranosyl-(1→2)-[ß-D-xy-lopyranosyl-(1→3)]-ß-D-glucuronopyranosyl)-28-O-(ß-D-xylopyranosyl-(1→3)-[ß-D-xylopyranosyl-(1→4)]-α-L-rhamnopyranosyl-(1→2)-[3,4-di-(O-acetyl)-ß-D-quinovopyranosyl]-(1→4)-ß-D-fucopyranosyl)-quillaic acid A trisaccharide unit is linked to C-3 and a hexasaccharide to C-28 in this bisdesmosidic quillaic acid type saponin. The sugar identities, and linkages with respective 1H/13C connectivities were unambiguously identified by a combination of HMBC (cf. FIG. 7), HSQC (high resolution), HSQC-DEPT, HQQC, HSQC-TOCSY, and DQF-COSY, $^1$H/$^1$H-TOCSY, $^1$H/$^1$H-NOESY, and non-decoupled HSQC. The $^1$J CH-connectivities of all sugar methin atoms were clearly derived by HSQC recorded with high resolution in the indirect dimension (TD: F2 1024, F1 2048).

The trisaccharide linked to C-3 consist of a glucuronic acid where the free carboxylic acid function at C-6 was not detected by $^{13}$C nor by HMBC, a galactose, and a xylose with anomeric resonances at δH/δC in [ppm] and $^3$J HH/$^1$J CH in [Hz]: β-GlcA-1 (δ 4.42, 104.6; d, 7.4, 161), β-Gal-1 (δ 4.80, 103.7; d, 7.8, 163), β-Xyl-1 (δ 4.57, 104.9; d, 7.8, 162). The pentasaccharide unit at C-28 consist of β-Fuc-1 (δ 5.29, 94.8; d, 7.8, 166), α-Rha-1 (δ 5.36, 101.5; d, 1.4, 171), β-Xyl'-1 (δ 4.49, 107.0; d, 7.2, 159), β-Qui-1 (δ 4.61, 105.8; d, 8.2, 161), β-Xyl"-1 (δ 4.51, 105.6; d, 7.0, 162).

Stereochemical properties of the glycosidic linkages were determined by characteristic values of $^3$J HH and $^1$J CH coupling constants J (Hz), respectively. A large trans-diaxial coupling ($^3$J HH: 7-8 Hz) for H-1/H-2 in case of glucose and galactose type sugars define a β-configuration. Characteristic $^1$J CH coupling values indicate the anomeric configuration of hexopyranoses with ~170 Hz for an α, and ~160 Hz for a β configuration. The detected values were in absolute accordance to these literature data and can also be applied for the quinovose (6-deoxy-glc), fucose (6-deoxygal) and rhamnose (6-deoxy-mannose).

The $^1$J CH coupling values J in [Hz] for the anomers were directly derived from the HMBC. In the $^1$H NMR of GE1741, the so-called 'bulk area' with non-anomeric protons occurred in the range 3.15-3.95 ppm, partly four to five sugar proton signals overlapped. $^3$J HH methin proton coupling pattern in the different sugar ring systems were detected and extracted by a non-decoupled HSQC experiment measured in the highly crowded signal range ($^1$H: δ 3.15-3.95 ppm, and $^{13}$C: δ 60-90 ppm where $^1$J CH and almost all $^3$J HH coupling constants were visualized and accurately determined. The non-decoupled HSQC clearly distinguished and elucidated GlcA from a possible GalA linked to C-3 seen by a large trans-diaxial coupling pattern of J 8.0 Hz (triplet) of GlcA-H-4 (δ 3.55 ppm) to H-3 and H-5. Also the TOCSY signal GlcA-H-1 (4.42 ppm) (spin-lock time: 50 ms), and the HSQC-TOCSY detected the position GlcA-5 indicating large coupling constants in this spin-system.

The identified anomer 1H signals were used as 'structural-reporter groups' (Vliegenthart, 2006), (Bubb, 2003), (Duus et al., 2000)). All independent spin-systems with scalar couplings in the existing 'bulk region' (δH: 3.15-4.7 ppm) in the oligosaccharide chains of GE1741 were elucidated by a combination of DQF-COSY, $^1$H/$^1$H-TOCSY, and were confirmed by a HSQC-TOCSY experiment. The long-range HMBC correlation signals (cf. FIG. 7) clearly identified the interglycosidic connecting points, e.g. connection to C-28 (δ 177.1) seen by Fuc-H-1 (δ 5.29), and the sequence and linkages of the branched pentasaccharide units with the central sugar unit Fucose: Fuc-H-4 (δ 3.76) to Qui-C-1 (δ 105.8), Fuc-H-2 (δ 3.79) to Rha-C-1 (δ 101.5), Rha-H-4 (δ 3.51) to Xyl'-C-1 (δ 107.0), and Xyl'-H-4 (δ 3.52) to Xyl"-C-1 (δ 105.6).

The two significant acetylation shifts observed for Qui-H-3 (δ 5.01) and Qui-H-4 (δ 4.63) clearly indicated the acetylation in the quinovose and moved the sugar methin resonances out of the 'proton bulk region'. The two points of acetylation were clearly elucidated by $^{2,3}$J CH long range cross-signals in the HMBC (cf. FIG. 7 from Qui-H-3 and Qui-H-4 to the acetate carbonyl functions (δ 172.1, 171.6). This double acetylation in the quinovose unit of GE1741 was unexpected and can be seen as a relevant structural feature and possibly as an important factor for the high activity of this saponin in the conducted assays.

The connection of the branched trisaccharide unit starting at glucuronic acid is seen by the $^{2,3}$J CH from GlcA-H-1 (δ 4.42) to C-3 (δ 86.4), and vice versa from H-3 (δ 3.86) to GlcA-H-1. Galactose is linked to GlcA seen by $^{2,3}$J CH from GlcA-H-2 (δ 3.64) to Gal-C-1 (δ 103.7) and vice-versa by Gal-H-1 (δ 4.80) to Fuc-C-2 (δ 75.1). The xylose is bound to GlcA-C-3 seen by $^{2,3}$J CH of Xyl-H-1 (δ 4.57) to GlcA-C-3 (δ 86.6), and in vice versa direction from Glc-H-3 to Xyl-C-1. The inter-glycosidic connectivities were also partly seen in the NOESY showing the through-space interaction over the glycosidic bonds. All structure relevant $^{2,3}$J CH long-range signals in the sugar units are presented in FIG. 7.

Transfection Efficiencies of *Gypsophila elegans* M. Bieb. Saponins

The transfection efficiency from crude extracts, via several purification steps through to the isolated saponin GE1741, was determined. All tested saponins increased the transfection efficiency significantly compared to a solely application of PD nanoplexes. The seed and root extract yielded comparable transfection efficiencies (~40%). However a lower concentration was used for the root extract (5 µg/mL). P2 implied a significantly higher transfection enhancing potential (72%) compared to P3 (29%) and P4 (27%). GE1741, which was isolated from P2, achieved a remarkable efficiency with 60% transfected cells.

These results are shown in FIG. 6 depicting the transfection efficiency of nanoplexes±triterpene saponins in Neuro2a cells. Biological activities of different purification steps were investigated until the final isolation of GE1741. P2, which was obtained after HPLC purification of the raw extract, achieved the highest efficiency, even exceeding the isolated GE1741. An asterisk (*) marks results being significant to the transfection method without GE1741 co-application as determined by a t-test with $p<0.05$ and $n≥3$.

Delivery of Nucleic Acids

Figure 8:
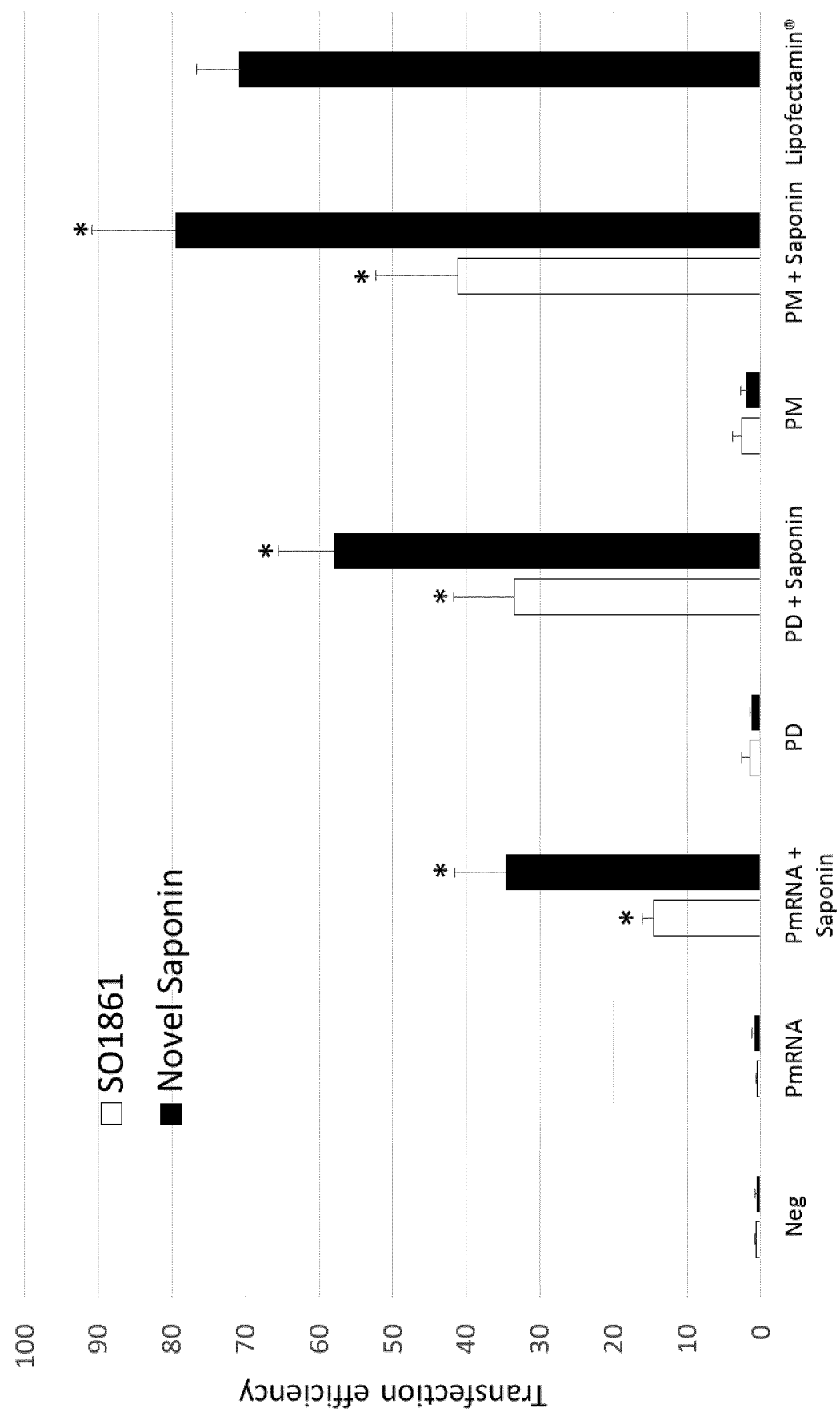
FIG. 8 shows a plot on the transfection efficiency of different transfection enhancers.

FIG. 8 compares the enhancement of the transfection efficiency by GE1741 ("novel saponin") with the enhancement of the transfection efficiency by a prior art saponin (SO1861) as well as the current "gold standard" Lipofectamin.

As negative control, Neuro2a cells have been incubated without an addition of particles comprising a nucleic acid.

Upon adding particles comprising a peptide bound to mRNA (PmRNA), a transfection efficiency in the single-digit range could be observed. After adding saponin as enhancer to the respective cell suspension, the transfection efficiency could be increased to approximately 15% when using SO1861, but to even 35% when using GE1741.

When incubating Neuro2a cells with particles comprising a peptide bound to DNA (PD), once again a transfection efficiency in the single-digit range could be observed. When SO1861 was added to the according solution, the transfection efficiency was increased to approximately 35%. If GE1741 was used instead of SO1861, a transfection efficiency of almost 60% could be observed.

When incubating Neuro2a cells with nanoparticles comprising a peptide bound to minicircle DNA (PM), once again a transfection efficiency in the single-digit area could be observed. After adding SO1861 to the according cell suspension, the transfection efficiency could be increased to more than 40%. If, on the other hand, GE1741 was added to the cell suspension, the transfection efficiency was increased to almost 80%.

A transfection efficiency of almost 80% when using peptide minicircle DNA nanoparticles is even better than a transfection efficiency of approximately 70% observed for the "gold standard" Lipofectamin. Thus, GE1741 is not only better than previously isolated saponins, but shows an even higher enhancement of the transfection efficiency than the gold standard being currently on the market.

The asterisks in FIG. 8 indicate a significant difference to the transfection method without saponin co-application by applying a t-test ($p<0.05$, $n≥3$).

Combination of GE1741 with Commercial Transfection Methods

Figure 9:
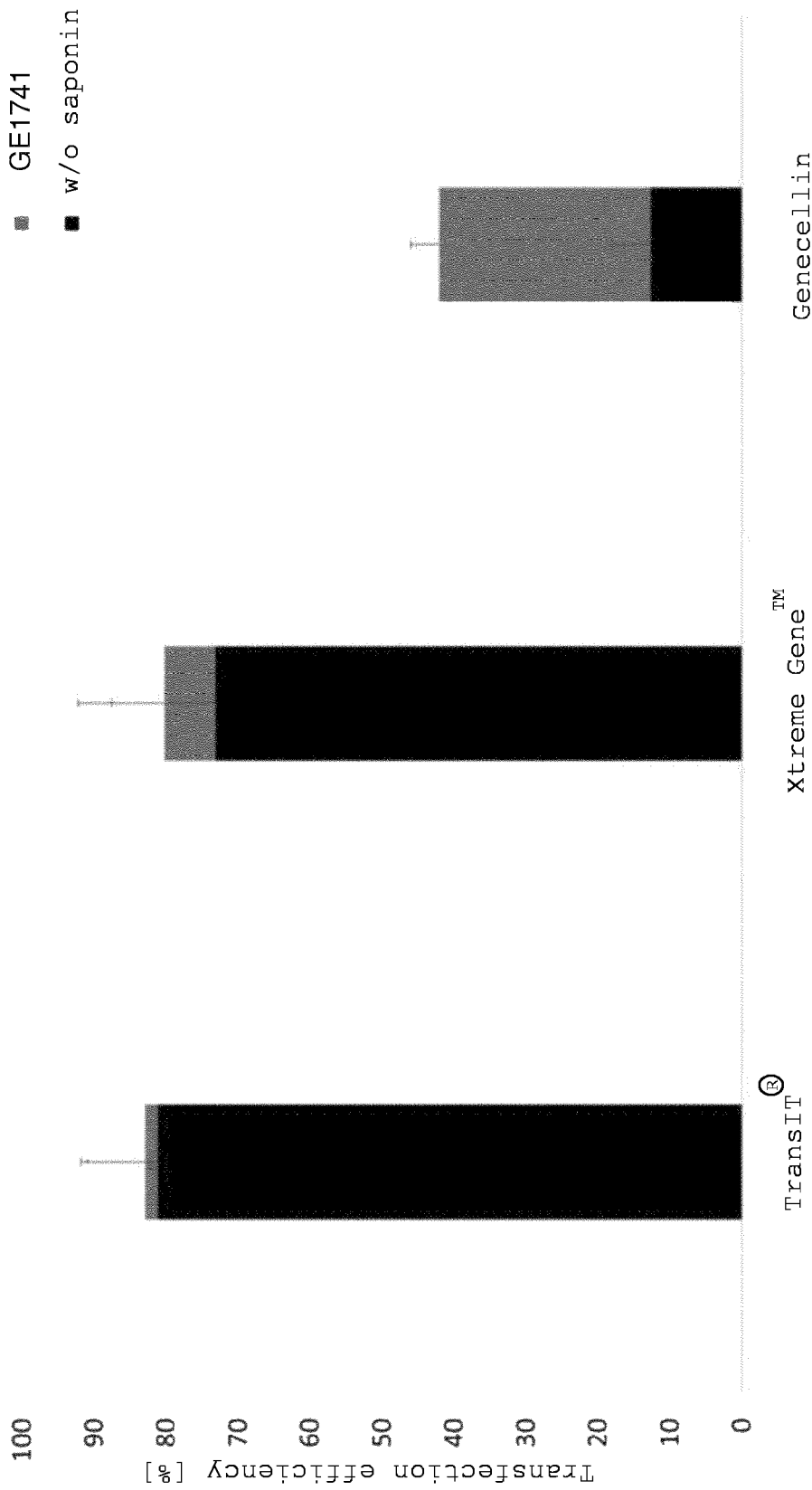
FIG. 9 shows the impact on GE1741 on the transfection efficiency of different commercial transfection methods.

HCT-116 cells were transfected with commercial transfection reagents in order to examine the impact of GE1741 on the transfection efficiency. The results are shown in FIG. 9. The addition of GE1741 led to an increase in transfection efficiency of each transfection method. While the transfection efficiency with TransIT was only slightly increased by 3 percentage points and that of Xtreme Gene by 8 percentage points, GE1741 boosted the transfection efficiency of Genecellin by 30 percentage points from 12% (without GE1741) to 42% (with GE1741).

Cell Toxicity and Permeability of GE1741

The impedance, which shows a direct correlation with cell viability, was investigated in order to determine the toxicity and the permeabilizing properties of GE1741.

Figure 10:
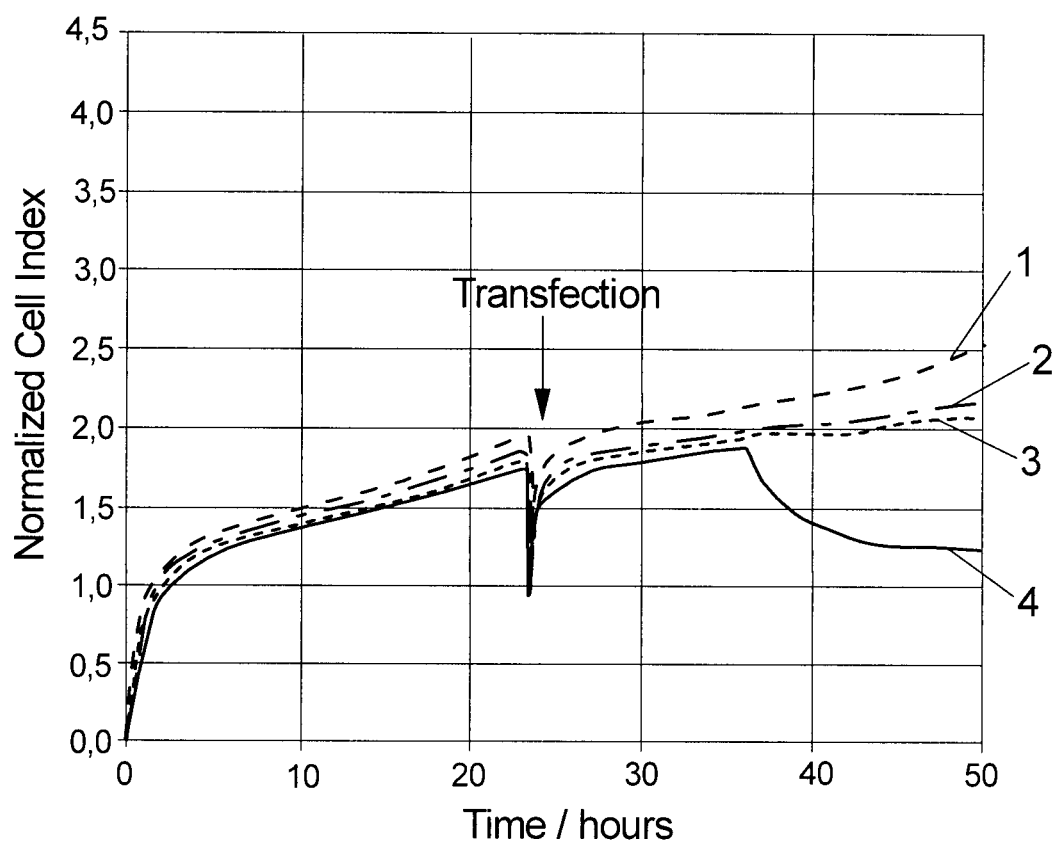
FIG. 10 shows the results of a first experiment for examining the toxicity of GE1741 on Neuro2a cells.
Figure 11:
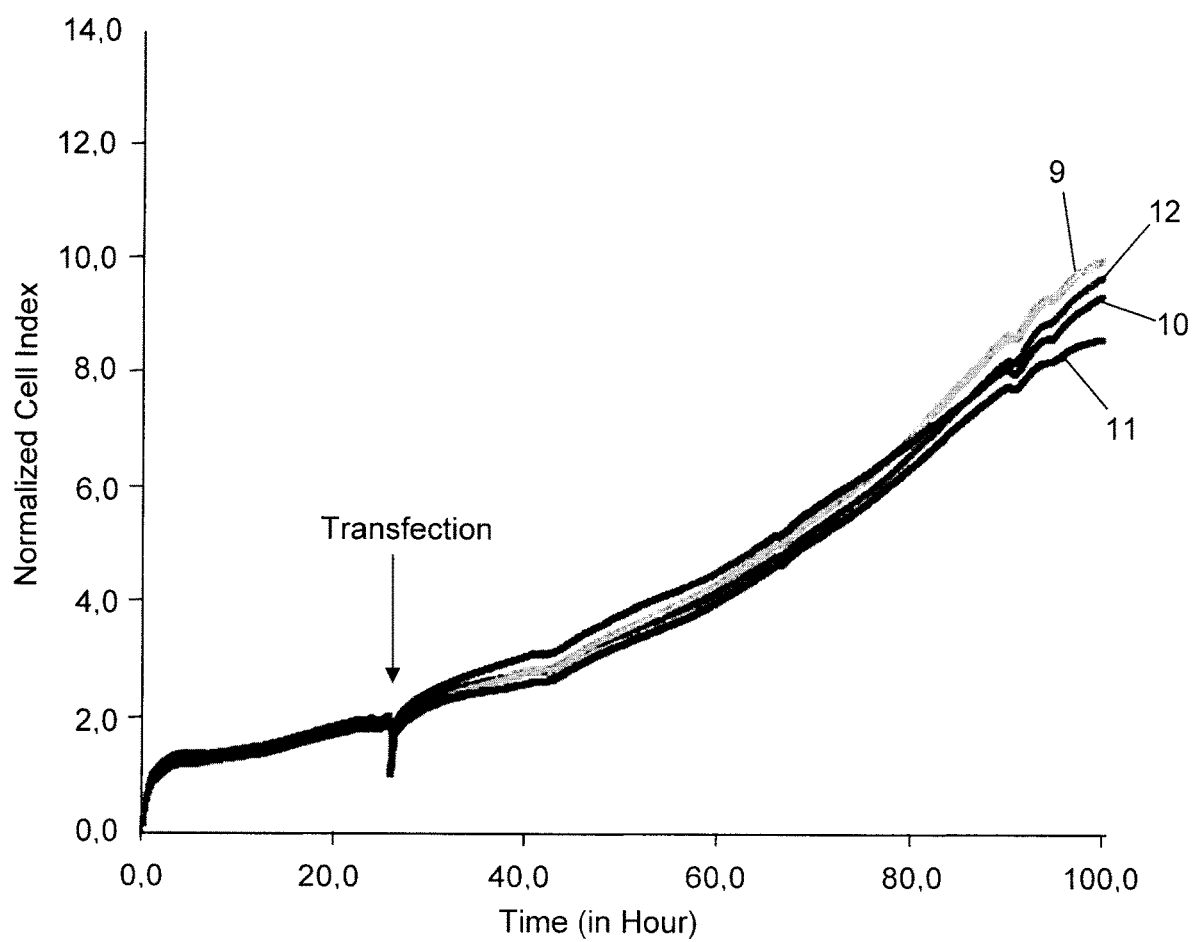
FIG. 11 shows results of a second experiment for examining the toxicity of GE1741 on Neuro2a cells and FIG. 12 shows the results of a targeted suicide gene therapy.

GE1741 does not exhibit cell-toxic effects when used in a concentration that is fully sufficient for enhancing the transfection efficiency. To test the toxic effects of GE1741, this saponin was applied in different concentrations to Neuro2a cells and incubated over a period of 50 hours. At concentrations of 2.5 µg/mL and 6.25 µg/mL, a normalized cell index is (within the error of measurement) identical to the normalized cell index observed for the negative control that has been subjected to a transfection process without an addition of GE1741. This is indicated in FIG. 10 by other three overlaid curves 1. If the GE1741 concentration is increased to 12.5 µg/mL, a slightly decreased normalized cell index could be observed (curve 2). The normalized cell index slightly further decreased upon increasing the GE1741 concentration to 25 µg/mL (curve 3).

A significant effect on the cell viability could only be observed at a GE1741 concentration of 50 µg/mL (curve 4). In this case, the normalized cell index markedly decreased approximately 12 hours after transfection.

Since an enhancement of the transfection efficiency could already be observed at a GE1741 concentration of 2 µg/mL (this concentration was used in the experiments the results of which are shown, e. g, in FIGS. 5 and 8), it can be concluded that GE1741 exhibits no cytotoxic effects in the relevant concentration range.

In another toxicity experiment, DNA nanoparticles (curve 9), DNA nanoparticles with 2 µg/mL GE1741 (GE1741; curve 10) or 2 µg/mL GE1741 alone (curve 11) was added to Neuro2a cells. Thereby, the DNA nanoparticles comprised DNA encoding for the Green Fluorescent Protein (GFP). Buffer was used as negative control (curve 12). After adding the respective substances to the cells at the time point marked with an arrow and the word "transfection", no significant difference in the cell viability could be observed. Thus, no toxic effects were revealed for any of the tested substances.

Transfection Efficiency

Figure 12:
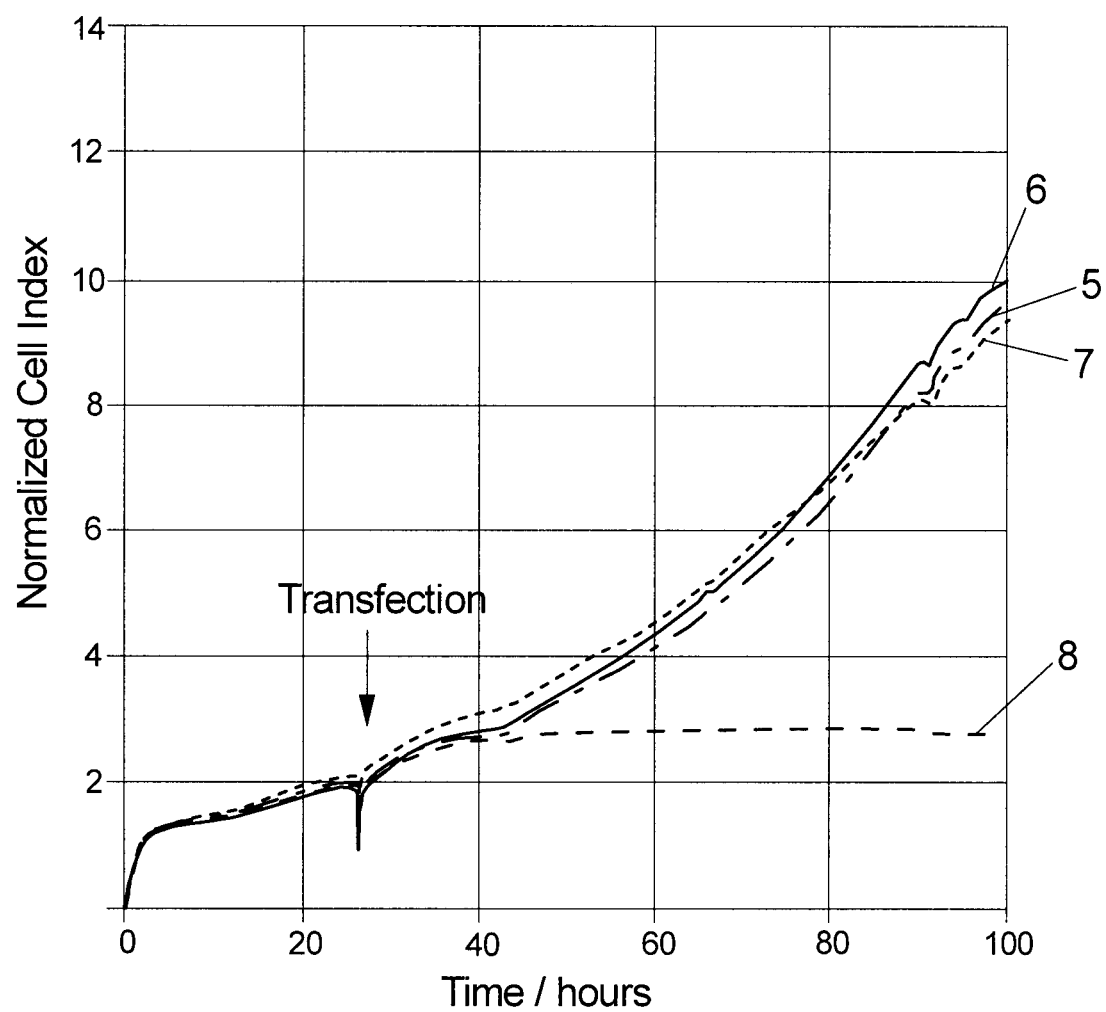

The transfection efficiency of GE1741 was also examined by transfecting cells with DNA encoding saporin. Saporin is a cytotoxic protein. If the transfection is successful, the transfected cells will die. The corresponding results are shown in FIG. 12. The negative control (curve 5) refers to Neuro2a cells incubated without any peptide DNA nanoparticles. Curve 6 refers to a transfection experiment of Neuro2a cells with nanoparticles comprising DNA encoding for saporin. The normalized cell index for this setup approximately corresponds to the normalized cell index of the negative control, indicating a very poor transfection efficiency. A likewise high normalized cell index could be observed if peptide DNA nanoparticles comprising DNA encoding for the green fluorescent protein were added to the cells together with 2 µg/mL GE1741. As shown in the previous Figures, such combination of peptide DNA nanoparticles and GE1741 serves for a highly efficient transfection. Since GFP is non-toxic for Neuro2a cells, the normalized cell index of this experimental setup (curve 7) roughly corresponds to the normalized cell index of the negative control (curve 5).

If, however, peptide DNA nanoparticles comprising DNA encoding for saporin are added together with 2 µg/mL GE1741 to Neuro2a cells, no further cell growth could be observed at approximately 15 hours after transfection (curve 8). Rather, the normalized cell index remains on a value below 3 that is considerable lower than in case of the negative control. This clearly shows the highly efficient transfection of the Neuro2a cells with DNA encoding for the cytotoxic protein saporin.

Summarizing, new transfection enhancing compounds could be identified by using a bioassay-guided isolation strategy on the mostly unexplored plant *Gypsophila elegans* M. Bieb. With this strategy, an alternating approach of purification and activity tests was conducted to find the highest active compound for advanced biochemical experiments. The HPLC chromatogram of the raw root extract revealed a number of peaks at a notable retention time, which were directly tested on a peptide-based transfection method. The distinct transfection enhancing effect of P2, compared to lower levels of P3 and P4, led to the assumption of a highly active compound in the specific fraction. The further purification and isolation via LC/MS and the identification of GE1741 via MS/MS provided a compound, the strong activity of which was confirmed. The lower efficiency of GE1741 towards P2 could be explained by the presence of a saponin mixture in P2 comprising, besides GE1741, a saponin the terminal xylose residue of which is replaced by arabinose.

The universal applicability of GE1741 in transfection experiments was investigated. A delivery of different nucleic acids, incorporated into nanoplexes, could be considerably increased. mRNA transfections were less effective than DNA transfections due to a faster degradation by cellular enzymes. However, a missing transcription step allowed the highest efficiency even after 24 h incubation time and therefore representing a rapid transfection method. Minicircle transfection yielded the highest efficiency, presumably caused by the smaller size of minicircle-compared to plasmid DNA.

The impact of GE1741 on commercial transfection methods was evaluated in order to underline the universal and simple applicability. An increase of transfection efficiency could be achieved for each method. A particular significant increase could be achieved for Genecellin transfections.

A common problem and limitation for the use of transfection reagents in specific in vitro and in vivo experiments are the toxic effects, which often come along with the high efficiency. By conducting impedance measurements, representing the cell viability, GE1741-mediated transfections were analyzed in terms of toxicity. The results revealed that cells that are transfected with a combination of nanoplexes and GE1741 were as viable as the untreated negative control. The application of different GE1741 concentrations showed a toxicity starting above a concentration of 6.25 µg/mL and first lytic effects at a concentration of 50 µg/mL, indicated by a considerable impedance drop. As transfections efficiency measurements were conducted in a concentration of 2 µg/mL, ultimately, a high activity with no toxicity can be confirmed for GE1741.

GE1741 is a novel and valuable compound for the process of saponin-mediated transfection, the so-called sapofection.

LIST OF PUBLICATIONS CITED IN THE PRECEDING SECTIONS

Findeisen, M.; Brand, T.; Berger, S., A 1H-NMR thermometer suitable for cryoprobes. Magn Reson Chem 2007, 45 (2), 175-8.
Piantini, U.; Sorensen, O. W.; Ernst, R. R. Multiple quantum filters for elucidating NMR coupling networks. *Journal of the American Chemical Society* 1982, 104, 6800-6801.
Bax, A.; Davis, D. G. Practical aspects of two-dimensional transverse NOE spectroscopy. *Journal of Magnetic Resonance* (1969) 1985, 63, 207-213.
Braunschweiler, L.; Ernst, R. R. Coherence transfer by isotropic mixing: Application to proton correlation spectroscopy. *Journal of Magnetic Resonance* (1969) 1983, 53, 521-528.
Jeener, J.; Meier, B. H.; Bachmann, P.; Ernst, R. R. Investigation of exchange processes by two-dimensional NMR spectroscopy. *The Journal of Chemical Physics* 1979, 71, 4546-4553
Bodenhausen, G.; Ruben, D. J. Natural abundance nitrogen-15 NMR by enhanced heteronuclear spectroscopy. *Chemical Physics Letters* 1980, 69, 185-189.
Kessler, H.; Schmieder, P.; Kock, M.; Reggelin, M. Selection of methyl resonances in proton-detected heteronuclear shift correlation, the HQQC experiment. *Journal of Magnetic Resonance* (1969) 1991, 91, 375-379.
Kessler, H.; Schmieder, P.; Kurz, M. Implementation of the DEPT sequence in inverse shift correlation; the DEPT-HMQC. *Journal of Magnetic Resonance* (1969) 1989, 85, 400-405.
Bax, A.; Subramanian, S. Sensitivity-enhanced two-dimensional heteronuclear shift correlation NMR spectroscopy. *Journal of Magnetic Resonance* (1969) 1986, 67, 565-569.
Cicero, D. O.; Barbato, G.; Bazzo, R. Sensitivity enhancement of a two-dimensional experiment for the measurement of heteronuclear long-range coupling constants, by a new scheme of coherence selection by gradients. *Journal of magnetic resonance* (San Diego, Calif.: 1997) 2001, 148, 209-213.
Bax, A.; Summers, M. F. Proton and carbon-13 assignments from sensitivity-enhanced detection of heteronuclear multiple-bond connectivity by 2D multiple quantum NMR. *Journal of the American Chemical Society* 1986, 108, 2093-2094.

The invention claimed is:

1. A method for an in vitro delivery of a nucleic acid, a lipid, a peptide and/or a protein to a cell, the method comprising the step of incubating the cell with the nucleic acid, the lipid, the peptide and/or the protein with a saponin according to formula (I):

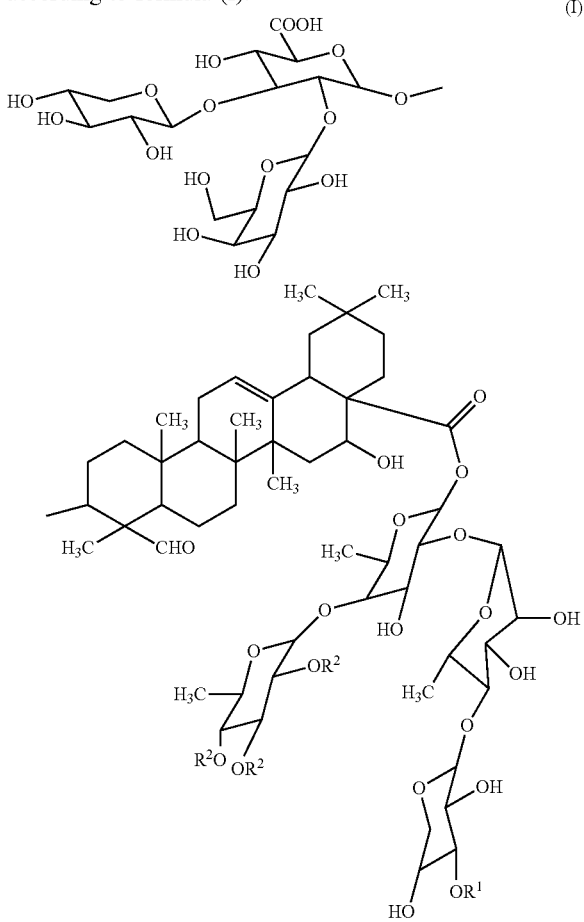

wherein
$R^1$ is a xylose residue or an arabinose residue bonded with its C1 atom to the corresponding xylose residue of formula (I); and
$R^2$ is independent from other $R^2$ residues in the same molecule H or an acetyl residue, with the proviso that at least two acetyl residues are present in the saponin.

2. The method according to claim 1, wherein the cell is a eukaryotic cell.

3. A transfection composition, comprising at least one transfection reagent chosen from the group consisting of liposomal-based transfection reagents and polymer-based transfection reagents as well as a saponin according to formula (I):

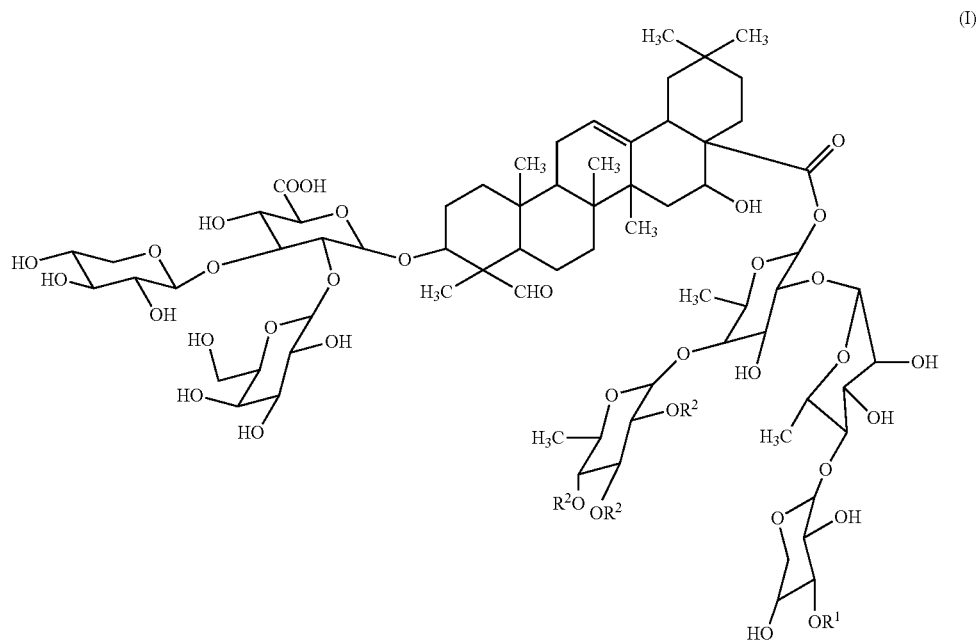

(I)

wherein
$R^1$ is a xylose residue or an arabinose residue bonded with its C1 atom to the corresponding xylose residue of formula (I); and
$R^2$ is independent from other $R^2$ residues in the same molecule H or an acetyl residue, with the proviso that at least two acetyl residues are present in the saponin.

4. The transfection composition according to claim 3, wherein $R^1$ is a xylose residue and/or the saponin carries exactly two acetyl groups.

5. The transfection composition according to claim 4, wherein the acetyl groups are bonded to the oxygen atoms in C3 and C4 position of the corresponding quinovose residue.

6. A method for an in vitro transfection, comprising the step of incubating a cell with a nucleic acid in the presence of a saponin according to formula (I):

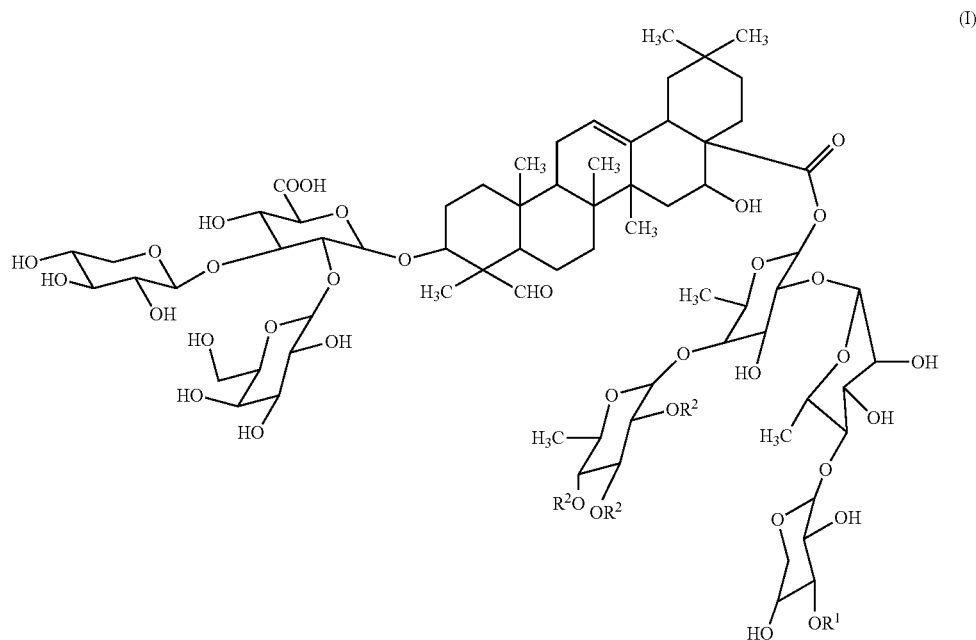

(I)

wherein
R¹ is a xylose residue or an arabinose residue bonded with its C1 atom to the corresponding xylose residue of formula (I); and
R² is independent from other R² residues in the same molecule H or an acetyl residue, with the proviso that at least two acetyl residues are present in the saponin.

7. The method according to claim 6, wherein the cell is a eukaryotic cell.

8. The method according to claim 6, wherein the nucleic acid forms part of a nanoparticle.

9. The method according to claim 6, wherein the saponin is used in a concentration lying in a range of 1 ng/mL to 25 ng/mL.

10. The method according to claim 6, wherein the saponin is used in combination with at least one transfection reagent chosen from the group consisting of liposomal-based transfection reagents and polymer-based transfection reagents.

11. A method for isolating a saponin according to formula (I):

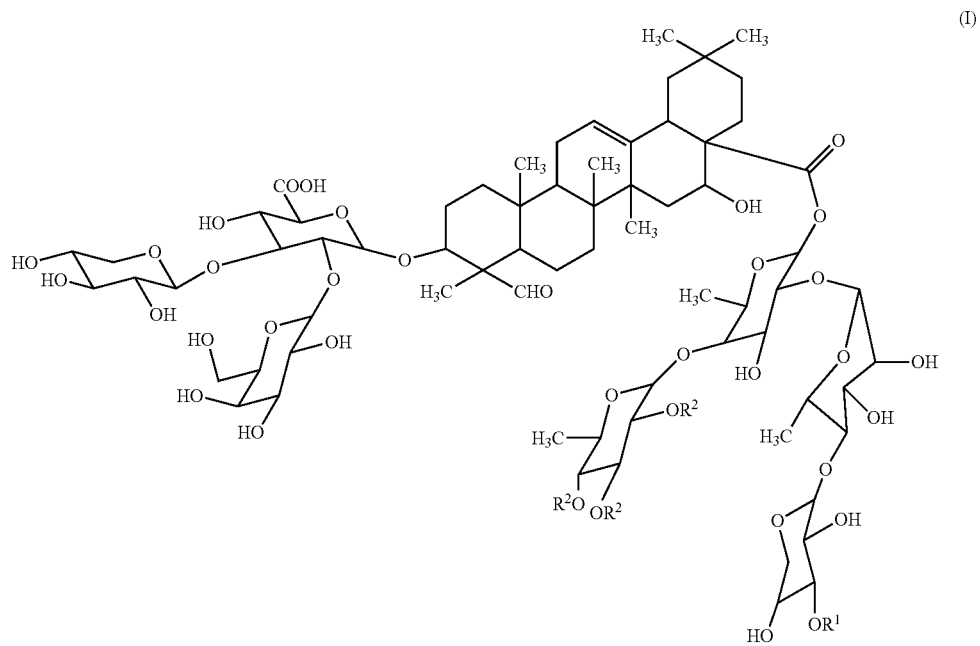

wherein
R¹ is a xylose residue or an arabinose residue bonded with its C1 atom to the corresponding xylose residue of formula (I); and
R² is independent from other R² residues in the same molecule H or an acetyl residue, with the proviso that at least two acetyl residues are present in the saponin from *Gypsophila elegans* M. Bieb, comprising the following steps:
cutting roots of *Gypsophila elegans* M. Bieb,
freeze-drying and grinding the cut roots to obtain a root powder,
extracting the root powder with a high-concentrated organic solvent to obtain a root extract,
removing the high-concentrated organic solvent from the root extract to obtain a dry extract,
dissolving the dry extract in a low-concentrated organic solvent to obtain an extract solution,
subjecting the extract solution to at least one chromatographic separation step to obtain a purified saponin solution, and
removing any solvent from the purified saponin solution to obtain a purified saponin powder.

* * * * *